(12) United States Patent
Chang

(10) Patent No.: US 11,141,599 B2
(45) Date of Patent: Oct. 12, 2021

(54) SYSTEMS, APPARATUS, AND METHODS FOR DOCUMENTING CODE BLUE SCENARIOS

(71) Applicant: LOS ANGELES BIOMEDICAL RESEARCH INSTITUTE AT HARBOR-UCLA MEDICAL CENTER, Torrance, CA (US)

(72) Inventor: Ruey-Kang Chang, Diamond Bar, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 360 days.

(21) Appl. No.: 15/974,367

(22) Filed: May 8, 2018

(65) Prior Publication Data
US 2018/0250519 A1    Sep. 6, 2018

Related U.S. Application Data

(63) Continuation-in-part of application No. 15/669,449, filed on Aug. 4, 2017, which is a continuation of
(Continued)

(51) Int. Cl.
*A61N 1/39*     (2006.01)
*A61B 5/113*    (2006.01)
(Continued)

(52) U.S. Cl.
CPC .............. *A61N 1/3937* (2013.01); *A61B 5/08* (2013.01); *A61B 5/1135* (2013.01);
(Continued)

(58) Field of Classification Search
CPC .................. A61N 1/39044; A61N 1/3943
See application file for complete search history.

(56) References Cited

U.S. PATENT DOCUMENTS 8,222,888 B2    7/2012  David et al.
10,433,767 B2 * 10/2019  Richard ............... A61H 31/005
(Continued)

OTHER PUBLICATIONS

Wyllie, J., Bruinenberg, J., Roehr, C., Rudiger, M., Trevisanuto, D. and Urlesberger, B., 2015. European Resuscitation Council Guidelines for Resuscitation 2015. Resuscitation, 95(1-80). (Year: 2015).*
(Continued)

*Primary Examiner* — Lynsey C Eiseman
*Assistant Examiner* — Amanda L Steinberg
(74) *Attorney, Agent, or Firm* — Pillsbury Winthrop Shaw Pittman LLP

(57) ABSTRACT

An apparatus may be configured for providing feedback to caregivers during a code blue scenario when adhered to the chest of a subject undergoing resuscitation by sensing and transmitting information associated with the code blue scenario. Such information may include one or more of vital signs of the subject during resuscitation, information associated with chest movements of the subject during resuscitation, and audio information from an environment of the subject during resuscitation. One or more processors may generate real-time feedback for communication to the caregivers during the code blue scenario based on the sensed and transmitted information.

28 Claims, 7 Drawing Sheets

Related U.S. Application Data application No. 14/245,858, filed on Apr. 4, 2014, now Pat. No. 9,743,882.

(51) Int. Cl.

| | |
|---|---|
| *A61B 5/08* | (2006.01) |
| *A61B 5/00* | (2006.01) |
| *G16H 40/63* | (2018.01) |
| *A61H 31/00* | (2006.01) |
| *G16H 15/00* | (2018.01) |
| *G16H 40/67* | (2018.01) |
| *A61B 5/0205* | (2006.01) |
| *A61B 5/021* | (2006.01) |
| *A61M 16/04* | (2006.01) |
| *A61B 5/024* | (2006.01) |
| *A61B 5/01* | (2006.01) |
| *A61M 16/00* | (2006.01) |

(52) U.S. Cl.
CPC .......... *A61B 5/4848* (2013.01); *A61B 5/6823* (2013.01); *A61B 5/6833* (2013.01); *A61H 31/00* (2013.01); *A61H 31/005* (2013.01); *G16H 15/00* (2018.01); *G16H 40/63* (2018.01); *G16H 40/67* (2018.01); *A61B 5/01* (2013.01); *A61B 5/021* (2013.01); *A61B 5/024* (2013.01); *A61B 5/0205* (2013.01); *A61B 5/02055* (2013.01); *A61B 5/113* (2013.01); *A61B 2560/0214* (2013.01); *A61B 2560/0242* (2013.01); *A61B 2560/0412* (2013.01); *A61B 2560/0475* (2013.01); *A61B 2560/0493* (2013.01); *A61H 2031/002* (2013.01); *A61H 2201/1619* (2013.01); *A61H 2201/501* (2013.01); *A61H 2201/5007* (2013.01); *A61H 2201/5043* (2013.01); *A61H 2201/5048* (2013.01); *A61H 2201/5058* (2013.01); *A61H 2201/5084* (2013.01); *A61H 2201/5097* (2013.01); *A61H 2230/00* (2013.01); *A61H 2230/045* (2013.01); *A61H 2230/06* (2013.01); *A61H 2230/065* (2013.01); *A61H 2230/207* (2013.01); *A61H 2230/208* (2013.01); *A61H 2230/30* (2013.01); *A61H 2230/305* (2013.01); *A61H 2230/405* (2013.01); *A61H 2230/50* (2013.01); *A61H 2230/505* (2013.01); *A61H 2230/65* (2013.01); *A61M 16/022* (2017.08); *A61M 16/04* (2013.01); *A61M 2205/05* (2013.01); *A61M 2205/332* (2013.01); *A61M 2205/3368* (2013.01); *A61M 2205/3375* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/581* (2013.01); *A61M 2205/583* (2013.01); *A61M 2205/584* (2013.01); *A61M 2205/60* (2013.01); *A61M 2205/6072* (2013.01); *A61M 2205/8206* (2013.01); *A61M 2209/088* (2013.01); *A61M 2210/10* (2013.01); *A61M 2230/04* (2013.01); *A61M 2230/06* (2013.01); *A61M 2230/205* (2013.01); *A61M 2230/30* (2013.01); *A61M 2230/40* (2013.01); *A61M 2230/42* (2013.01); *A61M 2230/50* (2013.01); *A61M 2230/63* (2013.01); *A61M 2230/65* (2013.01); *A61N 1/3904* (2017.08)

(56) References Cited

U.S. PATENT DOCUMENTS

| | | | |
|---|---|---|---|
| 2003/0060723 A1 | 3/2003 | Joo et al. | |
| 2004/0116969 A1 | 6/2004 | Owen et al. | |
| 2005/0055242 A1 | 3/2005 | Bello et al. | |
| 2005/0251213 A1* | 11/2005 | Freeman | G06F 19/00 607/5 |
| 2005/0251214 A1 | 11/2005 | Parascandola et al. | |
| 2005/0277872 A1 | 12/2005 | Colby, Jr. et al. | |
| 2006/0019229 A1 | 1/2006 | Morallee et al. | |
| 2006/0223042 A1 | 10/2006 | Epler et al. | |
| 2006/0270952 A1 | 11/2006 | Freeman et al. | |
| 2008/0089313 A1 | 4/2008 | Cayo et al. | |
| 2008/0171311 A1 | 7/2008 | Centen et al. | |
| 2008/0255428 A1 | 10/2008 | Sharda et al. | |
| 2008/0288026 A1 | 11/2008 | Cross et al. | |
| 2008/0312519 A1 | 12/2008 | Maschke | |
| 2008/0312565 A1 | 12/2008 | Celik-Butler et al. | |
| 2009/0055735 A1 | 2/2009 | Zaleski et al. | |
| 2009/0143045 A1 | 6/2009 | Graves et al. | |
| 2010/0114218 A1 | 5/2010 | Heath et al. | |
| 2011/0237924 A1* | 9/2011 | McGusty | A61B 5/04085 600/391 |
| 2011/0284004 A1 | 11/2011 | Silver et al. | |
| 2011/0295622 A1* | 12/2011 | Farooq | G16H 50/70 705/3 |
| 2012/0083720 A1 | 4/2012 | Centen et al. | |
| 2012/0123223 A1* | 5/2012 | Freeman | G16H 40/67 600/301 |
| 2012/0123224 A1 | 5/2012 | Packer et al. | |
| 2012/0136404 A1 | 5/2012 | Drew et al. | |
| 2012/0150058 A1 | 6/2012 | Zubrow | |
| 2012/0197324 A1 | 8/2012 | Nova | |
| 2012/0306662 A1 | 12/2012 | Vosch et al. | |
| 2012/0323591 A1 | 12/2012 | Bechtel et al. | |
| 2013/0046543 A1* | 2/2013 | Kitchens | H04M 3/493 704/270.1 |
| 2013/0120140 A1 | 5/2013 | Patil et al. | |
| 2013/0296719 A1* | 11/2013 | Packer | A61B 5/0205 600/484 |
| 2014/0358585 A1 | 12/2014 | Reiner | |
| 2015/0031961 A1 | 1/2015 | Freeman | |
| 2015/0065815 A1* | 3/2015 | Najarian | A61B 5/349 600/301 |
| 2015/0352369 A1* | 12/2015 | Quan | A61N 1/3937 607/7 |
| 2016/0135706 A1* | 5/2016 | Sullivan | A61B 5/1118 600/301 |
| 2017/0333722 A1 | 11/2017 | Chang | |

OTHER PUBLICATIONS

Patent Cooperation Treaty, International Search Report for PCT/US2019/031055, dated Aug. 16, 2019, pp. 1-3.
United States Patent and Trademark Office, Final Office Action issued in U.S. Appl. No. 15/669,449, dated Nov. 2, 2018, pp. 1-12.
United States Patent and Trademark Office, Office Action issued in U.S. Appl. No. 15/669,449, dated Oct. 30, 2020, pp. 1-19.
Au, "What Difference Does a Form Make: Redesign and Evaluation of a Form for Documenting In-Hospital Cardiac Arrest", Ph.D,University of Washington, 2013, pp. 1-153.
U.S. Patent and Trademark Office, Office Action issued in U.S. Appl.No. 15/669,449, dated May 14, 2020, pp. 1-24.
United States Patent and Trademark Office, Office Action issued in U.S. Appl. No. 15/669,449, filed Jun. 15, 2021.

\* cited by examiner

SYSTEMS, APPARATUS, AND METHODS FOR DOCUMENTING CODE BLUE SCENARIOS

CROSS REFERENCE TO RELATED APPLICATIONS

This application is a continuation in part of U.S. patent application Ser. No. 15/669,449 filed on Aug. 4, 2017, which is a continuation of U.S. patent application Ser. No. 14/245,858 filed on Apr. 4, 2014, both entitled "SYSTEMS, APPARATUS, AND METHODS FOR DOCUMENTING CODE BLUE SCENARIOS" and both incorporated herein by reference in their entireties.

GOVERNMENT FUNDING

This invention was made with government support under National Institutes of Health (National Institute of General Medical Sciences) grant number 1R41GM113463-01A1. The government may have certain rights in the invention.

FIELD OF THE DISCLOSURE

This disclosure relates to systems, apparatus, and methods for documenting a code blue scenario in which a subject is undergoing resuscitation.

BACKGROUND

Patient safety is one of the most important challenges facing today's healthcare. There are approximately 2.5 million deaths in the U.S. each year, about a third of which occur in acute care hospitals. Unless there are "do-not-resuscitate" advanced directives in place, patients who die in a hospital most likely have undergone one or more resuscitation attempts known as "code blue." Code blue is used by hospitals to describe a scenario in which a patient with cardiac or respiratory arrest requires stat medical intervention (i.e., resuscitation). Medical errors occur in healthcare every day. In code blue scenarios, medical errors may be likely to occur, which can cost lives. Common errors in cardiopulmonary resuscitation (CPR) may include slow chest compression rates, shallow chest compression depths, hyperventilation, long pauses in CPR before shock delivery, delivery of electrical defibrillation for nonshockable rhythms, medication errors, failure to follow resuscitation guidelines (e.g., advanced cardiovascular life support (ACLS), pediatric advanced life support (PALS), and/or other guidelines), and/or other errors.

Studies have found conventional paper-based documentation practices of code blue scenarios may be inaccurate, often misreporting intervention delivery times, missing their delivery entirely, and/or making other documentation errors. Paper-based code blue records may commonly have missing time data, include use of multiple timepieces for recording time data during the same event, and convey a wide variation in coherence and precision of clocking devices. For example, the documentation of time in emergency events has been shown to vary significantly, by as much as nineteen minutes, depending on which clocking devices are used. Furthermore, incomplete and inaccurate documentation of code blue scenarios are frequently a source for medicolegal disputes.

SUMMARY

Exemplary implementations may provide feedback (e.g., coaching) to caregivers during a code blue scenario, as well as complete and accurate documentation of code blue scenarios, which may facilitate quality improvement of resuscitation in practice, enhance in patent safety, and protect healthcare professionals against lawsuits. Some implementations provide an electronic apparatus for providing feedback to caregivers and complete documentation of code blue scenarios. This apparatus may be referred to as a "BlueBox." According to one implementation, the apparatus may include a five by ten centimeter elongated patch configured to be placed next to the mid-sternum on the left. Other configurations are contemplated. The apparatus may be configured to provide feedback to caregivers related to, as well as provide complete capture of, all code blue events including vital signs of a subject (e.g., a patient or other individual undergoing resuscitation), cardiac rhythm, verbal orders, execution of the orders, chest compression, cardioversion/defibrillation, procedures, medications, labs, and/or other events. The apparatus may enhance the safety of subjects undergoing CPR. The apparatus may provide electronic code blue records that can be useful for electronic medical record (EMR) documentation, education, and quality improvement.

The apparatus may include multiple sensors embedded in a micro-electronics platform. The sensors may include electrocardiogram (ECG) sensors, one or more accelerometers (e.g., a tri-axial accelerometer), a temperature sensor, an impendence sensor, one or more acoustic sensors, one or more sensors configured for detecting oxygen saturation ($SpO_2$) (e.g., pulse oximeter sensors), and/or other sensors. In some implementations, all of the sensors may be integrated into a volume with a four centimeter diameter and eight millimeter thickness. Feedback may be given, and vital signs and audio information may be simultaneously recorded with corresponding time stamps and/or other information. Security measures may be implemented to protect the recorded information. An enclosure and contact surface of the apparatus may be designed to withstand pressure from chest compressions and/or voltages from cardioversion and defibrillation.

An "electronic code blue sheet" and/or feedback user interface may be provided to display the feedback, and/or the code blue events recorded by the apparatus. In accordance with some implementations, the user interface may be provided by an app suitable for one or more platforms including Apple iOS™ platform, Android™ platform, Microsoft Windows™, and/or other platforms. The app may run on one or more computing platforms associated with a caregiver, a medical facility and/or other medical providers, medical equipment in the environment where the code blue events occur, and/or other computing platforms. The app may receive information from sensors of the apparatus, retrieve information recorded by the apparatus, receive and/or retrieve information from a server and/or other processing devices, and/or perform other operations via a wireless connection, and automatically display the feedback, the code blue events chronologically with time stamps, and/or other information, in some implementations. The user interface may provide zoomable views of the feedback, the vital signs, and/or other information. The user interface may facilitate communication of audio instructions, playback of other audio information, and/or other operations. In some implementations, a trained transcriptionist may annotate additional events, such as procedures and medications, based on the voice recordings. This annotation may be performed automatically with the aid of voice recognition technology, in some implementations. The electronic code blue sheet may be exported (e.g., as a portable document file (PDF) and/or other electronic document formats) so that the code blue sheet can be printed for paper medical record, or for uploading to EMR.

One aspect of the disclosure relates to an apparatus configured to provide feedback to caregivers during a code blue scenario. The apparatus may comprise an enclosure, a sensor bank, a feedback interface, one or more processors, and/or other components. The enclosure may be adhered to a chest of a subject undergoing resuscitation. The enclosure may be configured to withstand compressive forces applied to the subject's chest from chest compressions during resuscitation. Components disposed within the enclosure may be protected from mechanical damage, electrical shock, and/or other conditions. The sensor bank may be at least partially disposed within the enclosure. The sensor bank may be configured to provide signals conveying information associated with the code blue scenario. The information may include vital signs of the subject during resuscitation, information associated with chest movements of the subject during resuscitation, audio information from an environment surrounding the subject during resuscitation, and/or other information. The feedback interface may be coupled with the enclosure. The feedback interface may be configured to provide real-time feedback to the caregivers during the code blue scenario. The real-time feedback may comprise a recommendation to begin resuscitation, adjustments that should be made to ongoing resuscitation, and/or other feedback. The one or more processors may be operatively coupled with the sensor bank and the feedback interface, one or more computing platforms, and/or other components. The one or more processors may be configured by computer program instructions to generate the real-time feedback based on the information in the signals from the sensor bank. In some implementations, the feedback may be provided by one or more components of the feedback interface, the user interface provided by the app described above, and/or other components.

In some implementations, the feedback interface may comprise one or more of a display screen, one or more indicator lights, a speaker, components for communication with one or more computing platforms, and/or other components. The feedback interface may be configured to provide the real-time feedback to the caregivers via one or more of the display screen, the one or more indicator lights, the speaker, the app running on the one or more computing platforms, and/or the other components. In some implementations, the feedback interface may include a timer. The timer may be activated responsive to one or both of the apparatus being removably adhered to the subject's chest or an adhesive cover being removed from the enclosure.

In some implementations, the real-time feedback may comprise adjustments that should be made to ongoing resuscitation such as recommended changes to one or more of a compression rate, a compression depth, a pause between compressions, or a compression interval of cardiopulmonary resuscitation (CPR) chest compressions performed on the subject during the code blue scenario. In some implementations, generating the real-time feedback based on the information in the signals from the sensor bank may comprise determining time elapsed since collapse of the subject. The time elapsed since collapse may be determined responsive to the information in the signals from the sensor bank indicating ventricular fibrillation and no respiratory movement, and/or other information. In some implementations, the real-time feedback may comprise a recommendation to begin chest compressions on the subject. In some implementations, the real-time feedback may comprise a recommendation to shock or defibrillate the subject. In some implementations, the real-time feedback may comprise a recommendation to inject the subject with epinephrine.

Another aspect of the disclosure relates to a method for providing feedback to caregivers during a code blue scenario with a feedback apparatus. The apparatus may comprise an enclosure, a sensor bank, a feedback interface, one or more processors, and/or other components. The method may comprise adhering the enclosure to a chest of a subject undergoing resuscitation. The enclosure may be configured to withstand compressive forces applied to the subject's chest from chest compressions during resuscitation. Components disposed within the enclosure may be protected from mechanical damage, electrical shock, and/or other conditions. The sensor bank may be at least partially disposed within the enclosure. The method may comprise providing, with the sensor bank, signals conveying information associated with the code blue scenario. The information may include vital signs of the subject during resuscitation, information associated with chest movements of the subject during resuscitation, audio information from an environment surrounding the subject during resuscitation, and/or other information. The feedback interface may be coupled with the enclosure. The method may comprise providing, with the feedback interface, real-time feedback to the caregivers during the code blue scenario. The real-time feedback may comprise a recommendation to begin resuscitation, adjustments that should be made to ongoing resuscitation, and/or other feedback. The one or more processors may be operatively coupled with the sensor bank and the feedback interface. The one or more processors may be configured by computer program instructions. The method may comprise generating, with the one or more processors, the real-time feedback based on the information in the signals from the sensor bank.

In some implementations, the feedback interface may comprise one or more of a display screen, one or more indicator lights, a speaker, components for communication with one or more computing platforms, and/or other components. The method may comprise providing the real-time feedback to the caregivers via one or more of the display screen, the one or more indicator lights, the speaker, the app described above, and/or the other components. In some implementations, the feedback interface may include a timer. The method may comprise activating the timer responsive to one or both of the apparatus being removably adhered to the subject's chest or an adhesive cover being removed from the enclosure.

In some implementations, the real-time feedback may comprise adjustments that should be made to ongoing resuscitation such as recommended changes to one or more of a compression rate, a compression depth, a pause between compressions, or a compression interval of cardiopulmonary resuscitation (CPR) chest compressions performed on the subject during the code blue scenario. In some implementations, generating the real-time feedback based on the information in the signals from the sensor bank may comprise determining time elapsed since collapse of the subject. The time elapsed since collapse may be determined responsive to the information in the signals from the sensor bank indicating ventricular fibrillation and no respiratory movement, and/or other information. In some implementations, the real-time feedback may comprise a recommendation to begin chest compressions on the subject. In some implementations, the real-time feedback may comprise a recommendation to shock or defibrillate the subject. In some implementations, the real-time feedback may comprise a recommendation to inject the subject with epinephrine.

Another aspect of the disclosure relates to an apparatus configured for documenting a code blue scenario when adhered to the chest of a subject undergoing resuscitation. The apparatus may comprise an enclosure and a sensor bank. The enclosure may be configured to withstand compressive forces applied to the subject's chest during resuscitation of the subject such that components disposed within the enclosure are protected from mechanical damage. The sensor bank may be at least partially disposed within the enclosure. The sensor bank may be configured to provide signals conveying information associated with a code blue scenario. The information may include vital signs of the subject during resuscitation and audio information from an environment surrounding the subject during resuscitation.

Another aspect of the disclosure relates to a system configured for documenting code blue scenarios. The system may comprise one or more physical processors configured to receive information from an apparatus configured for documenting a code blue scenario when adhered to the chest of a subject undergoing resuscitation by sensing and transmitting information associated with the code blue scenario. The information may include vital signs of the subject during resuscitation and audio information from an environment of the subject during resuscitation. The one or more physical processors may be disposed at a location other than the apparatus. The one or more processors may be further configured to execute computer program instructions. The computer program instructions may comprise a code blue documentation component configured to provide code blue documentation that conveys information related to the vital signs of the subject during resuscitation and the audio information from the environment of the subject during resuscitation.

Another aspect of the disclosure relates to a method for documenting code blue scenarios. The method may comprise receiving, using one or more physical processors, vital sign information associated with vital signs of a subject during resuscitation in a code blue scenario. The vital sign information may be received from an apparatus configured to be adhered to the chest of the subject when the code blue scenario begins. The method may comprise receiving, using one or more physical processors, audio information from an environment surrounding the subject during resuscitation. The audio information may be received from the apparatus. The method may comprise providing, using one or more physical processors, code blue documentation that conveys information related to the resuscitation performed on the subject. The code blue documentation may be based on both the vital sign information and the audio information.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
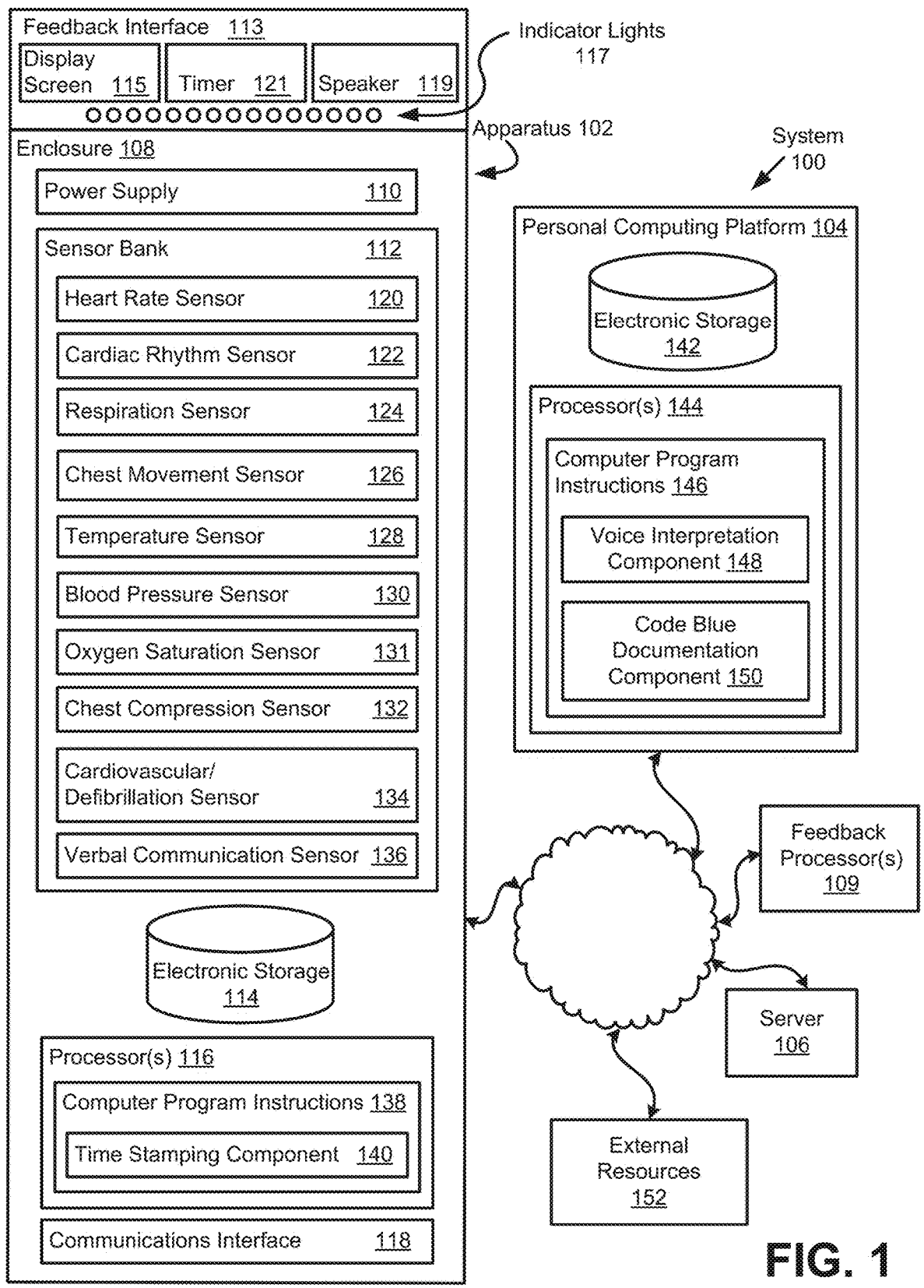
FIG. 1 illustrates a system configured to provide feedback to caregivers during code blue scenarios, as well as document the code blue scenarios, in accordance with one or more implementations.

FIG. 1 illustrates a system 100 configured for providing feedback to caregivers during code blue scenarios, as well as documenting code blue scenarios, in accordance with one or more implementations. The feedback (e.g., coaching) provided to caregivers during a code blue scenario, as well as complete and accurate documentation of code blue scenarios, may facilitate quality improvement of resuscitation in practice, enhance in patent safety, and protect healthcare professionals against lawsuits. The system 100 may provide complete documentation for code blue scenarios, which may be useful for EMR integration, medical education, quality improvement, medicolegal purposes, and/or other purposes. The system 100 may provide standardized code blue documentation that is complete and operator-independent, thus improving quality of care and protecting patient safety. According to some implementations, system 100, with its capacity to provide feedback and capture most or all events in code blue scenarios, may provide much needed assistance to healthcare professionals who lead code blue teams (e.g., anesthesiologists, intensivists, emergency physicians, and/or other healthcare professionals).

Components of system 100 may continuously record important vital parameters of a subject undergoing CPR, procedures such as chest compression and defibrillation, and all verbal communications among the code blue team members such as orders, responses, medications, lab results, and/or other verbal communications. Proper documentation of code blue scenarios may facilitate detailed reviews of CPR events for quality improvement, thus enhancing patent safety. Proper documentation may protect healthcare professionals against lawsuits which might otherwise be due to incomplete or inaccurate documentation. Properly documenting care in a patient's medical records is essential and, in the event of a lawsuit, provides evidence that the care that was provided met professional standards.

In one exemplary implementation, system 100 may include an apparatus shaped as a disk having a diameter of four centimeters and a thickness of one centimeter, housed in a ten by five centimeter patch shaped as a big Band-Aid. The apparatus may be configured to be placed on the left mid chest, over the fourth intercostal space between the left sternal border and left nipple, at the beginning of a code blue scenario. There may be no control buttons or other mechanisms on the apparatus. Instead, the apparatus may power on and begin recording responsive to a protective cover being removed. This may be achieved using a magnetic switch, according to some implementations. The apparatus may power off and stop recording responsive to the apparatus being removed from the subject. The apparatus may be configured to prevent unauthorized removal of any internal memory and/or tampering with recorded information.

Figure 2:
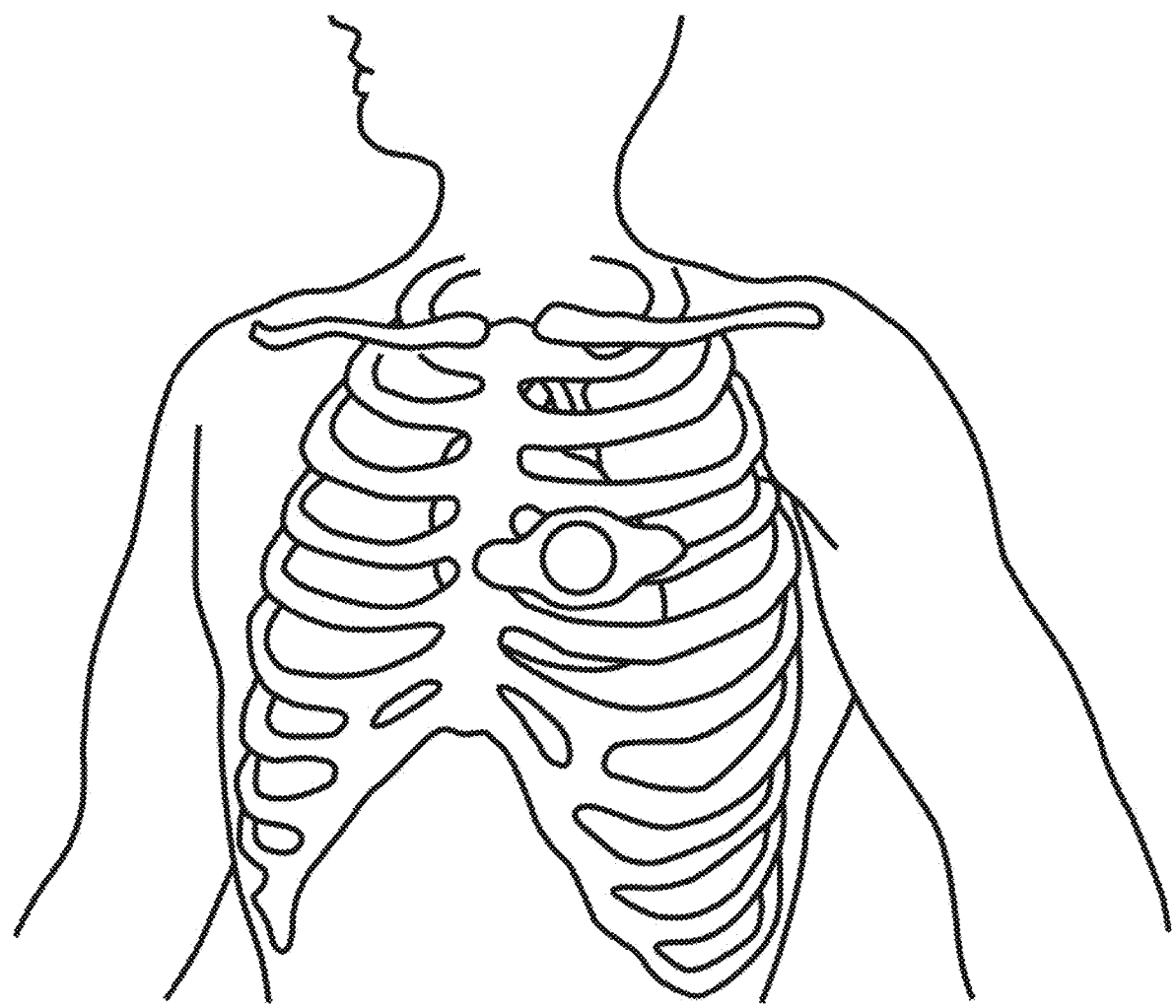
FIG. 2 illustrates an exemplary positioning of an apparatus configured for providing feedback during, and documenting, a code blue scenario when adhered to the chest of a subject undergoing resuscitation, in accordance with one or more implementations.

As depicted in FIG. 1, system 100 may include an apparatus 102, a personal computing platform 104, a server 106, one or more feedback processors 109, and/or other components. The apparatus 102 may be configured for providing feedback to caregivers during code blue scenarios, as well as documenting code blue scenarios when adhered to the chest of a subject undergoing resuscitation. FIG. 2 illustrates an exemplary positioning of an apparatus that is the same or similar to apparatus 102, in accordance with one or more implementations. The position of apparatus 102 depicted in FIG. 2 is not intended to be limiting as other positions are contemplated and are within the scope of the disclosure. For example, in some implementations, the position may be at a different location of the subject or covering a different shape or size area on the subject than that depicted in FIG. 2.

Referring again to FIG. 1, apparatus 102 may include an enclosure 108. The enclosure 108 may be configured to withstand compressive forces applied to the subject during resuscitation such that components disposed within enclosure 108 are protected from mechanical damage (e.g., breaking or otherwise becoming unable to operate properly due to receipt of compressive forces). The enclosure 108 may be configured to withstand electrical conditions (e.g., high voltages) resulting from defibrillation being performed on the subject such that component disposed within enclosure 108 are protected from electrical and/or magnetic damage (e.g., shorting or otherwise becoming unable to operate properly due to exposure to certain electrical conditions). The enclosure 108 may have an adhesive applied to an external portion of enclosure 108 to facilitate removably adhering to the subject's chest. The apparatus 102 may be prepared with a removable cover or film 111 that protects the adhesive on enclosure 108, and exposes the adhesive when removed.

Figure 3:
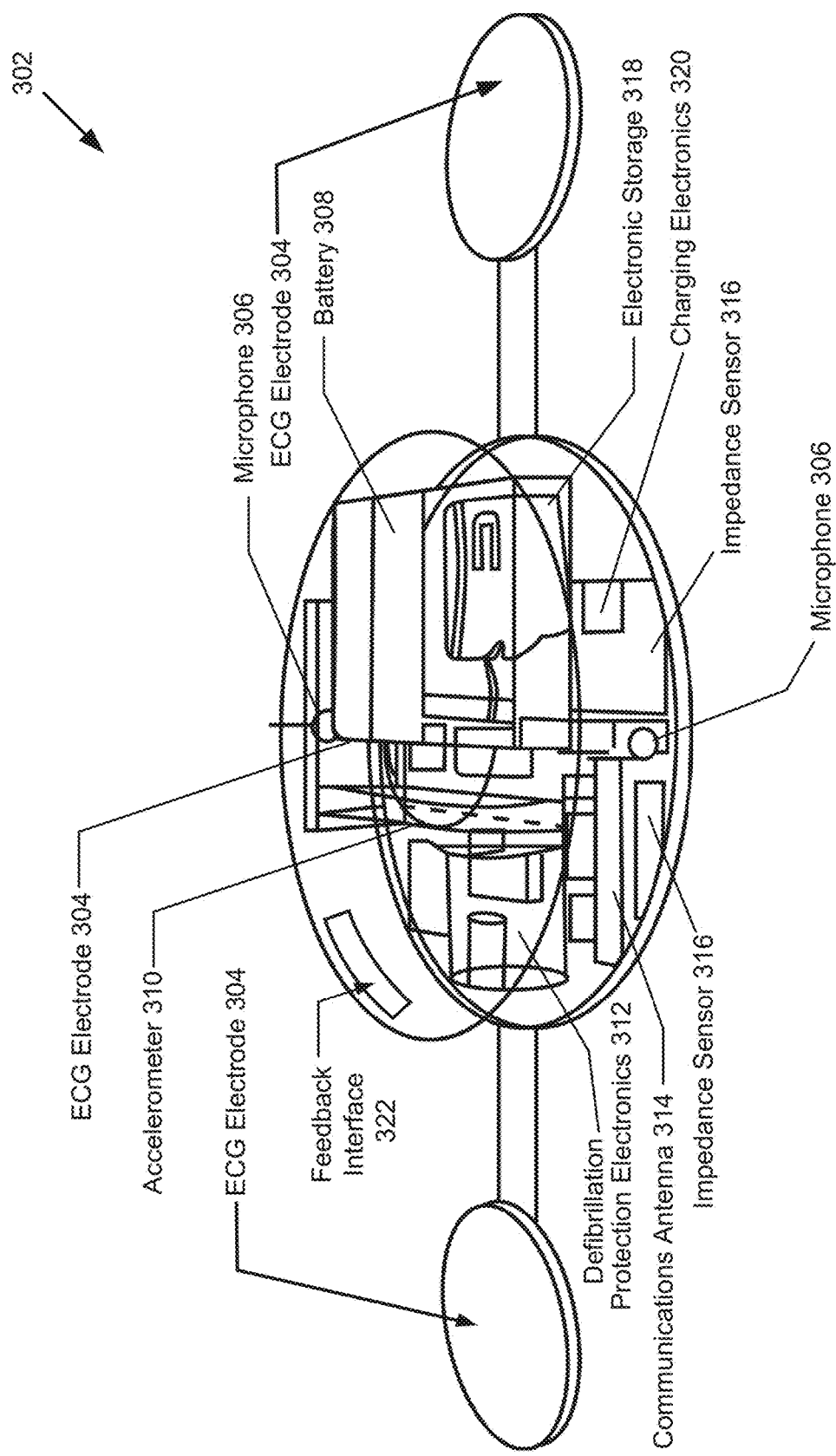
FIG. 3 illustrates an electronics hardware footprint and configuration of the apparatus, in accordance with one or more implementations.

FIG. 3 illustrates an electronics hardware footprint and configuration 302 of apparatus 102, in accordance with one or more implementations. The electronics hardware footprint and configuration 302 may include are area in which one or more components of apparatus 102 are disposed. As depicted in FIG. 3, electronics hardware footprint and configuration 302 may include one or more of ECG electrodes 304, microphones 306, a battery 308, an accelerometer 310, defibrillation protection electronics 312, communications antenna 314, impedance sensors 316, electronic storage 318, charging electronics 320, a feedback interface 322, and/or other components. In some implementations, there may be no physical buttons, physical switches, or plug-style ports associated with electronics hardware footprint and configuration 302. In some implementations, electronics hardware footprint and configuration 302 may include one or more indicator lights configured to convey feedback or a status of apparatus 100 (e.g., on, off, recording, not recording, and/or other statuses). In some embodiments, feedback interface 322 may include a display screen, one or more indicator lights, a speaker, one or more components (e.g., Bluetooth and/or other communication components) configured to communicate real-time and/or near real-time feedback to the caregivers during a code blue scenario via one or more computing platforms remote from the apparatus 102, and/or other electronic components configured to provide feedback to caregivers during a code blue scenario.

Other configurations for electronics hardware footprint and configuration 302 are contemplated. The positions of various components on electronics hardware footprint and configuration 302 may vary according to different implementations. The shape and/or size of electronics hardware footprint and configuration 302 depicted in FIG. 3 are not intended to be limiting as other shapes and/or sizes are contemplated and are within the scope of the disclosure. For example, in some implementations, the shape of electronics hardware footprint and configuration 302 may be more complex (e.g., more constituent shapes, curves, or angles) or less complex (e.g., less constituent shapes, curves, or angles) than that depicted in FIG. 3. In addition, there may be more or less sensor positions at the same or different locations on electronics hardware footprint 302. The size of electronics hardware footprint and configuration 302 may vary according to various factors includes a subject size (e.g., adult versus child), sensors sizes, and/or other factors.

Figure 4:
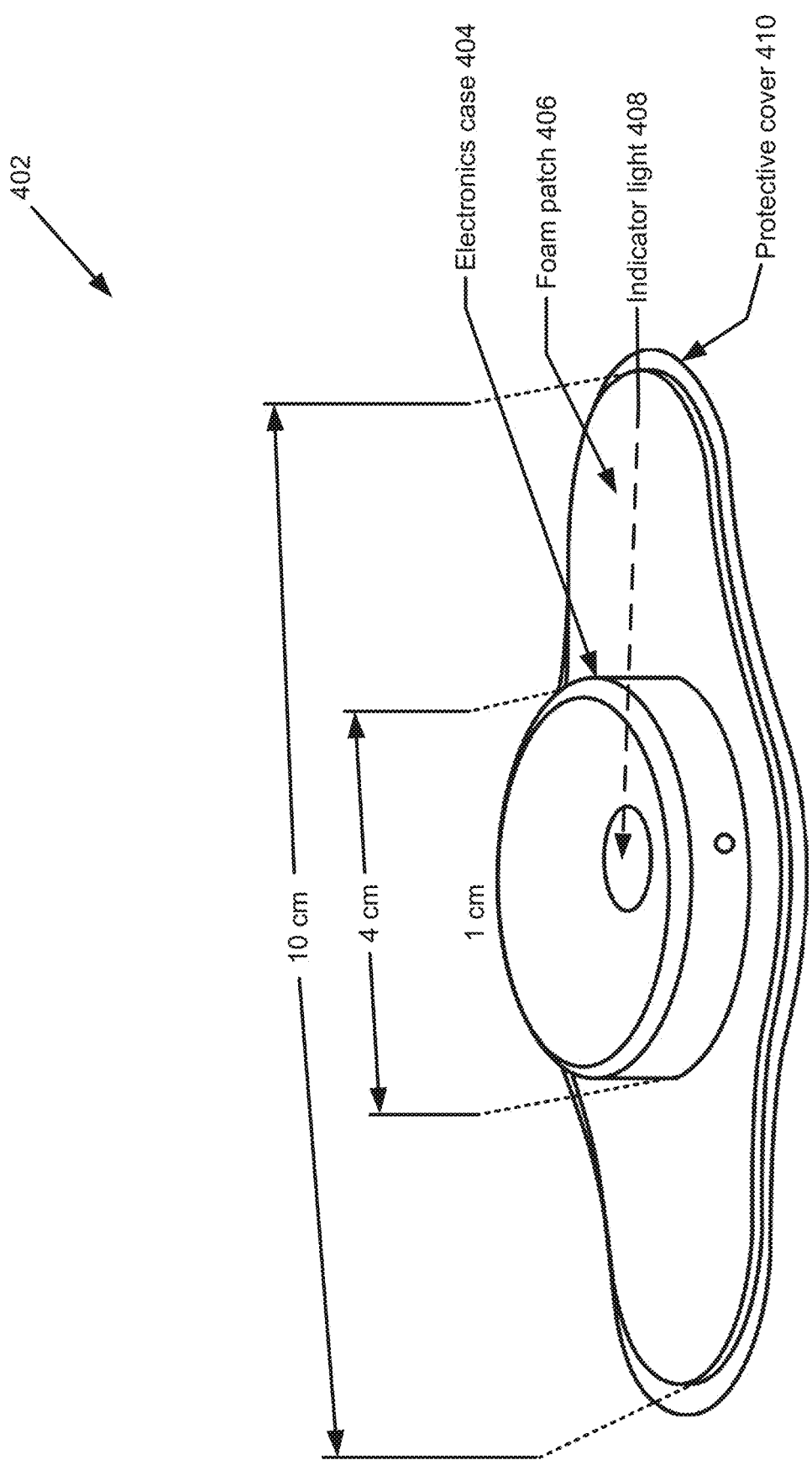
FIG. 4 illustrates an exemplary enclosure of the apparatus, in accordance with one or more implementations.

FIG. 4 illustrates an exemplary enclosure 402 of apparatus 102, in accordance with one or more implementations. The enclosure 402 may be similar to or the same as enclosure 108 described in connection with FIG. 1. The enclosure 402 may be configured to enclose some or all of electronics hardware footprint and configuration 302 (see FIG. 3). As depicted in FIG. 4, enclosure 402 may include one or more of an electronics case 404, a foam patch 406, an indicator light 408, a removable protective cover 410, and/or other components. The enclosure 402 may be made in whole or in part of one or more of acrylic, foam, plastic, metal, resin, and/or other materials. Pressure used for chest compressions may be up to 125 pounds. As such, enclosure 402 may be configured to withstand twenty or more pounds per square inch (PSI), or about 150 or more pounds of total force, according to some implementations. The enclosure 402 may include a hydrogel at a surface configured to contact skin on the subject. Such hydrogel may facilitate measurements by one or more of ECG sensors, temperature sensors, and/or other sensors. A surface of enclosure 402 may be configured to be adhered to skin of the subject. The removable protective cover 410 may cover an adhesive that facilitates adhesion by enclosure 402 to the subject. In some implementations, a magnetic switch (not depicted) may be included in enclosure 402 and be configured such that, responsive to a user removing the disposable cover and/or placing apparatus 102 on the subject, apparatus 102 may be powered on and/or collecting information associated with a code blue scenario.

Other configurations for enclosure 402 are contemplated. The shape and/or size of enclosure 402 depicted in FIG. 4 are not intended to be limiting as other shapes and/or sizes are contemplated and are within the scope of the disclosure. For example, in some implementations, the shape of enclosure 402 may be more complex (e.g., more constituent shapes, curves, or angles) or less complex (e.g., less constituent shapes, curves, or angles) than that depicted in FIG. 4. The size of enclosure 402 may vary according to various factors includes a subject size (e.g., adult versus child), sensors sizes, and/or other factors.

Referring again to FIG. 1, apparatus 102 may include one or more of a power supply 110, a sensor bank 112, a feedback interface 113, electronic storage 114, one or more processors 116, a communications interface 118, and/or other components.

The power supply 110 may be disposed within enclosure 108. The power supply 110 may be configured to provide electrical power to one or more components of apparatus 102. The power supply 110 may be configured to provide electrical power to one or more components of apparatus 100 responsive to one or both of apparatus 100 being removably adhered to a subject's chest or an adhesive cover being removed from enclosure 108. The power supply 110 may include one or more of a battery, a capacitor, and/or other power supplies. The power supply 110 may be replaceable. According to various implementations, power supply 110 may be rechargeable using a conductive wire line in or an inductive wireless mechanism.

The sensor bank 112 may be at least partially disposed within enclosure 108. The sensor bank 112 may be configured to provide signals conveying information associated with a code blue scenario. The information may include vital signs of the subject during resuscitation and/or audio information from an environment surrounding the subject during resuscitation. The audio information from the environment may include voice commands issued during resuscitation of the subject. The audio information from the environment may include a vocal indication of a vital sign (e.g., blood pressure, whether or not the subject has a pulse, etc.) of the subject during resuscitation.

In some implementations, sensor bank 112 may include one or more of a heart rate sensor 120, a cardiac rhythm sensor 122, a respiration sensor 124, a chest movement sensor 126, a temperature sensor 128, a blood pressure sensor 130, an oxygen saturation ($SpO_2$) sensor 131, a chest compression sensor 132, a cardioversion and/or defibrillation sensor 134, a verbal communication sensor 136, and/or other components.

The heart rate sensor 120 may be configured to provide a signal conveying information associated with a heart rate of the subject during resuscitation. By way of non-limiting example, the signal from heart rate sensor 120 may facilitate determining and/or presenting a heart rate of the subject, indications of when the subject's heart beats, and/or other information associated with the subjects heart function. In some implementations, heart rate sensor 120 may include one or more ECG sensors.

The cardiac rhythm sensor 122 may be configured to provide a signal conveying information associated with a cardiac rhythm of the subject during resuscitation. By way of non-limiting example, the signal from the cardiac rhythm sensor 122 may facilitate determining and/or presenting the subject's cardiac rhythm as shown by ECG, various types of arrhythmias (e.g., ventricular fibrillation), and/or other information associated with the subject's cardiac rhythm. In some implementations, cardiac rhythm sensor 122 may include one or more ECG sensors.

The respiration sensor 124 may be configured to provide a signal conveying information associated with a respiration of the subject during resuscitation. By way of non-limiting example, the signal from respiration sensor 124 may facilitate determining and/or presenting the subject's respiration rate, the subject's respiration volume, an indication of when the subject breaths, an indication of when a positive pressure ventilation was performed on the subject, an indication of how many positive pressure ventilations have been performed on the subject, an indication of a volume associated with positive pressure ventilations, and/or other information associated with the subject's breathing. In some implementations, respiration sensor 124 may include an impedance sensor.

The chest movement sensor 126 may be configured to provide a signal conveying information associated with chest movements caused by artificial respiration provided to the subject during resuscitation. By way of non-limiting example, the signal from chest movement sensor 126 may facilitate determining and/or presenting an indication of when an artificial breath was provided to the subject, and/or other information associated with artificial respiration provided to the subject. In some implementations, chest movement sensor 126 may include one or more accelerometers.

The temperature sensor 128 may be configured to provide a signal conveying information associated with a temperature of the subject during resuscitation. By way of non-limiting example, the signal provided by temperature sensor 128 may facilitate determining and/or presenting an indication of the subject's core temperature, the subject's surface temperature, a temperature of an environment surrounding the subject, a change in a temperature, and/or other information associated with temperature. In some implementations, temperature sensor 128 may include one or more of a thermometer, a thermistor, a thermocouple, and/or other temperature sensor.

The blood pressure sensor 130 may be configured to provide a signal conveying information associated with a blood pressure of the subject during resuscitation. In some implementations, blood pressure sensor 130 may be configured to receive a signal conveying information associated with a blood pressure of the subject during resuscitation from an external source. For example, blood pressure sensor 130 may receive a signal from a sphygmomanometer or blood pressure sensor (not depicted) that is separate and distinct from apparatus 102. As such, blood pressure sensor 130 may be communicatively coupled with a sphygmomanometer or blood pressure sensor. In some implementations, blood pressure sensor 130 may include a microphone configured to record verbal announcements of the subject's blood pressure.

The oxygen saturation sensor 131 may be configured to provide a signal conveying information associated with an oxygen saturation of the subject's blood. By way of non-limiting example, the signal provided by oxygen saturation sensor 131 may facilitate determining and/or presenting an indication of a saturation of peripheral oxygen ($SpO_2$) associated with the subject.

The chest compression sensor 132 may be configured to provide a signal conveying information associated with chest compressions performed on the subject during resuscitation. By way of non-limiting example, the signal provided by chest compression sensor 132 may facilitate determining and/or presenting an indication of when a chest compression was performed on the subject, an amount of force applied to the subject by a chest compression, a displacement (depth) of the subject's chest cause by a chest compression, a rate of successive chest compressions, a pause in successive chest compressions, and/or other information associated with chest compressions performed on the subject. In some implementations, chest compression sensor 132 may include one or more accelerometers.

The cardioversion and/or defibrillation sensor 134 may be configured to provide a signal conveying information associated with cardioversion procedures and/or defibrillation procedures performed on the subject during resuscitation. By way of non-limiting example, the signal provided by cardioversion and/or defibrillation sensor 134 may facilitate determining and/or presenting an indication of when cardioversion procedures and/or defibrillation procedures were performed on the subject, an amount of energy associated with cardioversion procedures and/or defibrillation procedures performed on the subject, duration of the energy, synchronized versus unsynchronized, subject's response to a cardioversion procedure and/or a defibrillation procedure, and/or other information associated with cardioversion procedures and/or defibrillation procedures. The cardioversion and/or defibrillation sensor 134 may be communicatively coupled to a cardioversion and/or defibrillation device. The cardioversion and/or defibrillation sensor 134 may be configured to sense electrical currents applied to the subject. The cardioversion and/or defibrillation sensor 134 may include one or more of an ECG sensor, an accelerometer, a microphone, and/or other sensors.

The verbal communication sensor 136 may be configured to provide a signal conveying information associated with verbal communication among the caregiver members of the code blue team, a response from a caregiver to an inquiry by apparatus 102 and/or feedback processor 109 (described below) in an environment of the subject during resuscitation, and/or other information. The verbal communication sensor 136 may include one or more of a microphone, an acoustic-to-electric transducer, and/or other sensor configured to sense audio information.

The feedback interface 113 may be coupled to, formed by, formed in, or otherwise attached to enclosure 108. In some implementations, the feedback interface 113 may be the same as or similar to feedback interface 322 (shown in FIG. 3 and described herein). In some implementations, the feedback interface 113 may include one or more components of communications interface 118 and/or have other components. The feedback interface 113 may comprise one or more of a display screen 115, one or more indicator lights 117 (which may or may not include the indicator light 408 described above), a speaker 119, and/or other components. The feedback may be provided to the caregivers via one or more of the display screen 115, the one or more indicator lights 117, the speaker 119, via personal computing platform 104, and/or other computing platforms, and/or other components.

In some embodiments, the feedback interface 113 may be at least partially formed in, on, or by a surface of enclosure 108 that is visible to the caregivers (e.g., a surface that is not adhered to the subject), and/or other surfaces. For example, the feedback interface 113 may be formed on a surface of enclosure 108 opposite a surface including a protective cover and/or adhesive of the system 100, on an edge surface of enclosure 108 visible to caregivers, and/or other surfaces. In some embodiments, one or more portions of the feedback interface 113 may be formed on different surfaces of enclosure 108. For example, the display screen 115, the speaker 119, and/or one or more indicator lights 117 may be formed on a larger surface of enclosure 108 opposite the protective cover, and one or more other indicator lights, and/or other components may be formed on a smaller edge surface of enclosure 108. It should be noted that this description of the feedback interface 113 is not to be considered limiting. The feedback interface 113 may or may not include all of the components listed above (e.g., the feedback interface 113 may comprise only indicator lights 117 and the speaker 119, only the indicator lights 117, only the display screen 115, only communications components of communications interface 118, etc.), and individual components may be located anywhere in, on, or otherwise coupled to enclosure 108 that allows the system 100 to function as described herein.

Feedback interface 113 may be configured to provide real-time and/or near real-time feedback to the caregivers during a code blue scenario. In some embodiments, the feedback may be provided in textual and/or graphical form via the display screen 115, via an app running on personal computing platform 104, and/or other components. In this example, the feedback may be provided by displaying textual instructions, displaying pictures and/or other images, and/or displaying other information. Displaying pictures and/or other images may include displaying annotated pictures or images that instruct (e.g., via arrows and/or other notations in the pictures and/or images) caregivers to perform specific actions, and/or other displays.

In some implementations, the feedback may be provided by lighting one more indicator lights 117 of different colors, lighting one or more indicator lights 117 with different patterns and/or frequencies, and/or by providing other lighting (e.g., lighting virtual lights displayed by the app running on personal computing platform 104). In this example, lights of different colors may correspond to different recommended actions, an intensity and/or other relative level of a recommended action (e.g., green means less intense, yellow means more intense, and red means most intense), and/or other information. A grid and/or other row(s) of lights may be lit in a specific shape or other pattern to indicate specific feedback. Lighting intensity (e.g., brightness) may be changed to indicate specific feedback. Indicator lights 117 may be controlled to blink or flash with specific patterns to indicate specific instructions.

In some implementations, the feedback may be provided by the speaker 119, speakers included in personal computing platform 104, and/or other sound generation components. In some implementations, the speaker 119, for example, may provide verbal commands and/or other instructions for caregivers. For example, the speaker may instruct a caregiver "begin CPR" or provide other commands. In some implementations, the speaker 119 may provide beeping sounds and/or other noises that correspond to specific actions, an intensity of the specific actions, and/or other information. For example, the speaker 119 may provide a first sound that indicates a caregiver should start CPR, and additional sounds that help the caregiver pace compressions. In this example, the speaker 119 may adjust an intensity (e.g., the volume) of the sounds to cause the caregiver to perform deeper or shallower compressions, or make other adjustments to the CPR provided.

In some implementations, the feedback interface 113 may be and/or include one or more components (e.g., communications interface 118) configured to communicate real-time and/or near real-time feedback to the caregivers during a code blue scenario via one or more computing platforms (e.g., personal computing platform 104) remote from the apparatus 102. For example, the feedback interface 113 may be and/or include one or more components configured to communicate feedback to caregivers via one or more personal computing platforms 104, one or more computing platforms associated with one or more items of medical equipment proximate to a location where a patient is undergoing resuscitation, one or more computing platforms configured to record and/or present medical records, one or more computing platforms associated with a medical services provider and/or care facility, and/or other computing platforms. For example, in some implementations, the feedback may be provided via Bluetooth components included in the feedback interface 113 linked to an iPad or other mobile device or computer. In some implementations, for example, the apparatus 102 itself may be able to process the analysis and provide feedback directly via one or more displays and/or indicators of the feedback interface 113 device (e.g., as described above). In some implementations, for example, the apparatus 102 may be coupled to a (e.g., cloud) server (e.g., server 106, feedback processor 109, etc.) and stream data to the server in real-time or near real-time, which may process received data, analyze results, and send them back to the apparatus 102 to show resuscitation recommendations. In some implementations, for example, the apparatus 102 may be coupled to the (e.g., cloud) server (e.g., server 106, feedback processor 109, etc.) and stream data to the server in real-time or near real-time, which may process received data, analyze results, and send them back to the personal computing platform 104 and/or other computing platforms to show resuscitation recommendations.

In some implementations, the feedback interface may include a timer 121. The timer 121 may be a display and/or other indication (e.g., a specific number of lit indicator lights 117 that steadily increase over time) of an elapsed amount of time. In some implementations, the timer 121 may be activated responsive to one or both of the apparatus 102 being removably adhered to the subject's chest or an adhesive cover being removed from the enclosure 102, for example. In some implementations, the timer 121 may be activated responsive to collapse of the subject, responsive to a start of CPR and/or other resuscitation operations, responsive to defibrillation, and/or responsive to other operations. In some implementations, as described below, the timer 121 may be activated by computer program instructions 138 and/or time stamping component 140.

The processor(s) 116 may be disposed within enclosure 108. The processor(s) 116 may be configured to execute computer program instructions 138. The computer program instructions 138 may include a time stamping component 140 and/or other components. The time stamping component 140 may be configured to time stamp signals provided by sensor bank 112, time stamp information conveyed by the signals provided by sensor bank 112, time stamp feedback determined by feedback processors 109 and/or provided by feedback interface 113, and/or other information. Such time stamps may facilitate chronological logging of code blue events including the feedback provided by the system 100.

The electronic storage 114 may be disposed within enclosure 108. The electronic storage 114 may be configured to store and provide access to information conveyed by the signals provided by sensor bank 112, information determined by feedback processor 109, and/or other information. According to some implementations, apparatus 102 may be assigned a unique serial number and a security code for accessing information stored by electronic storage 114. To access the stored information using a given personal computing device (e.g., personal computing platform 104), the given personal computing device may be required to be paired with apparatus 102 via a Bluetooth link and/or other communicative connection, in accordance with some implementations.

In some implementations, a patient's identifiers may be recorded by virtue of a user verbally identifying the patient's name, a hospital ID number, a date of birth, and/or other patient information. In some implementations, apparatus 102 may be configured to wirelessly retrieve information including patient information from other electronic medical devices. The apparatus 102 may be configured to obtain patient information by scanning visual marks (e.g., barcode, QR code, and/or other visual marks), by imaging the patient's ID band, by a keypad, and/or by other techniques.

The communications interface 118 may be disposed within enclosure 112. The communications interface 118 may be configured to communicate with one or more other components of system 110 by wireless connections and/or wired connections. The communication interface 118 may be configured to transmit one or more of signals provided by sensor bank 112, information conveyed by the signals provided by sensor bank 112, information stored by electronic storage 114, information received from feedback interface 113, information received from processor(s) 116, and/or other information. The communications interface 118 may be configured to receive information from one or more other components of system 100. For example, the communications interface 118 may be configured to receive feedback (and/or information related to the feedback) determined by feedback processor 109, transmit (e.g., via Bluetooth components, etc., as described herein) the information received from feedback processor 109 to personal computing platform 104 for communication to a caregiver, and/or perform other operations. In some implementations, the communications interface 118 may be configured to transmit received feedback to feedback interface 113 for provision to caregivers. According to some implementations, communications interface 118 may be compatible with one or more of a Bluetooth standard, a Wi-Fi standard, an ANT or ANT+ standard, a near-field standard, wireless data communication protocols, and/or other communications standards.

The feedback processor 109 may formed by and/or in one or more individual stand alone processors 109, one or more servers 106, one or more personal computing platforms 104, the apparatus 102, and/or other components of the system 100. The feedback processor 109 may be configured to generate real-time and/or near real-time feedback for caregivers based on the information in the signals from the sensor bank 112 and/or other information. The real-time and/or near real-time feedback may comprise a recommendation to begin resuscitation, adjustments that should be made to ongoing resuscitation, and/or other feedback. In some implementations, the generated real-time and/or near real-time feedback may comprise recommendations that one or more actions taken by taken by the code blue caregiver team during the code blue scenario such as recommending one or more of chest compressions be performed on the subject during resuscitation, cardioversion procedures and/or defibrillation procedures be performed on the subject during resuscitation, medications be administered to the subject during resuscitation, endotracheal intubation be performed on the subject, artificial respiration be provided to the subject during resuscitation, vascular accesses (e.g., intravenous lines, intra-osseous lines, arterial lines, and/or other accesses) be created, surgical procedures be performed, laboratory tests be performed, and/or other actions be taken by the code blue caregiver team.

By way of a non-limiting example, in some implementations, the feedback processor 109 may be configured such that the real-time feedback may comprise adjustments that should be made to ongoing resuscitation. Such adjustments may comprise recommended changes to one or more of a compression rate (e.g., compressions per minute), a compression depth (e.g., cm), a pause between compressions (e.g., sec), or a compression interval of cardiopulmonary resuscitation (CPR) chest compressions performed on the subject during the code blue scenario. For example, the rate and depth of chest compression may be detected based on output signals from the chest compression sensor 132. The feedback processor 109 may be configured to determine whether the rate and/or depth of chest compression are within a predetermined amount of a target rate and/or depth of chest compression and/or meet other target criteria. In some implementations, the predetermined amount may be an absolute value, a percentage, and/or other predetermined amounts. In some implementations, the feedback processor 109 may be configured to determine whether the rate and/or depth of chest compression are within a predetermined amount of 10%, 20%, 50%, and/or other percentages of the target rate and/or depth of chest compression. In some implementations, responsive to the rate and/or depth being more than 20% (for example) different than the target rate and/or depth, the feedback processor 109 may cause the feedback interface 113 to provide feedback to the caregiver performing CPR. The feedback processor 109 may control the speaker 119, the indicator lights 117, and/or other components of the feedback interface 113 to provide feedback to the caregiver that causes the caregiver to adjust the way the caregiver is performing CPR on the subject. In some implementations, the target rate and/or depth of chest compression may be determined at manufacture of the system 100, received and/or adjusted via input to the personal computing platform 104, determined by the feedback processor 109 and/or other components based on information from the external resources 152 and/or other sources, determined by the server 106, and/or determined in other ways.

In some implementations, generating the real-time feedback based on the information in the signals from the sensor bank may comprise determining time elapsed since a collapse of the subject. The time elapsed since a collapse may be determined to be at least some minimum amount of time. The feedback processor 109 may be configured to determine time elapsed since collapse responsive to the information in the signals from the sensor bank indicating ventricular fibrillation and no respiratory movement in the subject. In some implementations, this minimum amount of time may be about one minute. In some implementations, this minimum amount of time may be about two minutes. In some implementations, this minimum amount of time may be about three or more minutes.

In some implementations, the feedback processor 109 may be configured such that the real-time feedback may comprise a recommendation to begin chest compressions on the subject. The recommendation to begin chest compressions on the subject may be determined responsive to the time elapsed since collapse of the subject being at least one minute (for example) and/or another predetermined amount of time, the information in the signals from the sensor bank 112 indicating no respiratory movement, the information in the signals from the sensor bank 112 indicating no pulse in the subject, and/or other information. For example, the recommendation to begin chest compressions may be determined responsive to an ECG (e.g., part of sensor bank 112 as described herein) which shows ventricular fibrillation and respiration sensors (e.g., 124) and/or chest movement sensors (e.g., 126) that show no respiratory chest movement. In this example, the feedback processor 109 may cause the speaker 119 to ask a caregiver whether the subject has a pulse. If the caregiver responds that there is no pulse (detected by the verbal communication sensor 136), the feedback processor 109 may control the speaker 119, the indicator lights 117, and/or other components of the feedback interface 113 to recommend beginning chest compressions.

In some implementations, the feedback processor 109 may be configured such that the real-time feedback may comprise a recommendation to shock or defibrillate the subject. The recommendation to shock or defibrillate the subject may be determined responsive to a time elapsed since a start of chest compressions being at least three minutes (for example) and/or another predetermined amount of time, the information in the signals from the sensor bank 112 indicating ventricular fibrillation, the information in the signals from the sensor bank 112 indicating no pulse in the subject, and/or other information. For example, after three minutes (for example) of chest compressions (e.g., as detected by the chest compression sensor 132), an ECG rhythm may be detected (e.g., by the cardiac rhythm sensor 122). Responsive to the ECG rhythm remaining Ventricular tachycardia (Vtach)/Ventricular fibrillation (Vfib), the feedback processor 109 may cause the speaker 119 to ask a caregiver whether the subject has a pulse or determine whether there is a pulse based on output signals from the heart rate sensor 120. If the caregiver responds that there is no pulse (detected by the verbal communication sensor 136) or if the output signals do not show a pulse, the feedback processor 109 may control the speaker 119, the indicator lights 117, and/or other components of the feedback interface 113 to recommend shock or defibrillation.

In some implementations, the real-time feedback may comprise a recommendation to inject the subject with epinephrine. The recommendation to inject the subject with epinephrine may be determined responsive to a time elapsed since a start of chest compressions being at least five minutes (for example), the information in the signals from the sensor bank 112 indicating ventricular fibrillation, the information in the signals from the sensor bank 112 indicating no pulse in the subject, and/or other information. For example, after five minutes (for example) of chest compressions (e.g., as detected by the chest compression sensor 132), an ECG rhythm may be detected (e.g., by the cardiac rhythm sensor 122). Responsive to the ECG rhythm remaining Vtach/Vfib, the feedback processor 109 may cause the speaker 119 to ask a caregiver whether the subject has a pulse or determine whether there is a pulse based on output signals from the heart rate sensor 120. If the caregiver responds that there is no pulse (detected by the verbal communication sensor 136) or if the output signals do not show a pulse, the feedback processor 109 may control the speaker 119, the indicator lights 117, and/or other components of the feedback interface 113 to recommend injecting the subject with epinephrine.

In some implementations, the subject may be receiving positive pressure ventilation during the code blue scenario. In such implementations, the feedback processor 109 may be configured such that the real-time feedback may comprise a recommendation to adjust a ventilation pressure, a ventilation rate, and/or other ventilation parameters. The recommendation to adjust the ventilation pressure and/or the ventilation rate may be determined based on information in the signals from the sensor bank 112 related to a rate and depth of chest rise in the subject, and/or other information. For example, the rate and depth of chest rise may be detected based on output signals from the respiration sensor 124, the chest movement sensor 126, or other sensors. The feedback processor 109 may be configured to determine whether the rate and/or depth of chest rise are within a predetermined amount of a target rate and/or depth of chest rise and/or meet other target criteria. In some implementations, the predetermined amount may be an absolute value, a percentage, and/or other predetermined amounts (e.g., similar to those described above). In some implementations, responsive to the rate and/or depth being more than the predetermined amount different than the target rate and/or depth, the feedback processor 109 may cause the feedback interface 113 to provide feedback to the caregivers. The feedback processor 109 may control the speaker 119, the indicator lights 117, the display screen 115, and/or other components of the feedback interface 113 to provide feedback to the caregiver that causes the caregiver to adjust the way the ventilation is provided to the subject. In some implementations, the target rate and/or depth of chest rise is determined at manufacture of the system 100, received and/or adjusted via input to the personal computing platform 104, determined by the feedback processor 109 and/or other components based on information from external resources 152 and/or other sources, determined by the server 106, and/or determined in other ways.

In some implementations, the feedback processor 109 may be configured such that generating the real-time feedback based on the information in the signals from the sensor bank 112 may comprise a machine-learning and/or model based analysis of the information in the signals from the sensor bank 112. The machine-learning and/or model based analysis may comprise determining which future actions taken by caregivers during resuscitation would improve a likelihood of recovery from the code blue scenario by the subject and/or determining other information. The machine learning and/or model based analysis may comprise generating the real-time feedback based on the predictions and/or other operations.

In some implementations, the machine learning and/or model based analysis may comprise a model based portion configured to reduce complexity by efficiently solving well-known parts of the analysis, and a machine learning portion configured to discover solutions. In some implementations, the model based portion may be used to determine whether certain target variables, such as chest compression rate and depth, are within or out of predetermined recommended parameter ranges. In some implementations, the model based portion may be augmented by deep machine learning. In some implementations, the machine learning and/or model based analysis may include training based on information from several individual patients (e.g., 100's, 1000's, and/or 100000's of patients).

In some implementations, the machine learning and/or model based analysis comprises an offline training mode during which the feedback processor 109 obtains training data comprising information from prior code blue scenarios including information from the sensor bank 112, corresponding feedback provided to caregivers, corresponding outcome information for patients, and/or other information for training machine learning algorithms and/or other electronic models used in the analysis. In some implementations, the feedback processor 109 may be configured such that the machine learning and/or model based analysis is performed by one or more machine learning algorithms, one or more neutral networks, and/or other models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neutral unit itself) may have a threshold function such that the signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

As described herein, the machine learning and/or model based analysis may be performed by feedback processors 109 (e.g., stand alone devices, and/or included in the server 106, the personal computing platform 104 (e.g., an iPad and/or other personal computing platforms), and/or other devices) and/or other components based on information transmitted from the apparatus 102. Once analyzed, in some implementations, the personal computing platform 104 (e.g., iPad) may display the results and recommendations. Corresponding feedback information may be sent back to the apparatus 102 to be shown via indicator lights, and/or LCD screen, etc., communicated audibly, and/or communicated to a caregiver in other ways.

The personal computing platform 104 may include one or more of a smartphone, a tablet computer, a laptop computer, a desktop computer, and/or other personal computing platforms. In some implementations, the personal computing platform 104 may be associated with one or more individual caregivers. In some implementations, the personal computing platform 104 may be associated with a care facility and/or other entities that provide medical care. In some implementations, the personal computing platform 104 may be associated with a patient receiving resuscitation. The personal computing platform 104 may include one or more of electronic storage 142, one or more processors 144, and/or other components. The processor(s) 144 may be configured to execute computer program instructions 146. The computer program instructions 146 may include one or more of a voice interpretation component 148, a code blue documentation component 150, and/or other components.

The voice interpretation component 148 may be configured to interpret one or more of a vital sign of the subject during resuscitation presented as a function of time, an action taken by a code blue team during the code blue scenario, and/or other information. The interpretation may be based on audio information from the environment surrounding the subject during resuscitation. The code blue team may include one or more healthcare providers, individual ones being assigned different roles and/or functions.

The code blue documentation component 150 may be configured to provide code blue documentation that conveys information related to the vital signs of the subject during resuscitation and the audio information from the environment surrounding the subject during resuscitation. The code blue documentation may include one or more of (1) one or more vital signs of the subject during resuscitation presented as a function of time, (2) one or more actions taken by a code blue team during the code blue scenario, the code blue team including one or more healthcare providers, (3) information based on the audio information from the environment of the subject during resuscitation presented as a function of time, and/or other information.

The one or more vital signs presented by the code blue documentation may include one or more of a heart rate of the subject during resuscitation, a cardiac rhythm of the subject during resuscitation, a respiration of the subject during resuscitation, chest movements of the subject with respiration during resuscitation, a temperature of the subject during resuscitation, a blood pressure of the subject during resuscitation, oxygen saturation (e.g., $SpO_2$) of the subject during resuscitation, and/or other information associated with vital signs.

The one or more actions taken by the code blue team during the code blue scenario may include one or more of chest compressions performed on the subject during resuscitation, cardioversion procedures and/or defibrillation procedures performed on the subject during resuscitation, medications administered to the subject during resuscitation, endotracheal intubation, artificial respiration provided to the subject during resuscitation, vascular accesses (e.g., intravenous lines, intra-osseous lines, arterial lines, and/or other accesses), surgical procedures, laboratory test results associated with the subject, results from point-of-care devices associated with the subject, and/or other information associated with actions taken by the code blue team. In some implementations, these actions may be responsive to feedback determined by feedback processor 109 and delivered by feedback interface 113 as described herein.

The information based on the audio information from the environment of the subject during resuscitation may include one or more of verbal commands issued by a leader of the code blue team, verbal responses to commands issued by a leader of the code blue team and/or a request for information as part of feedback determination by feedback processor 109, chest compressions performed on the subject during resuscitation, cardioversion procedures and/or defibrillation procedures performed on the subject during resuscitation, verbal assessments of a status of the subject during resuscitation, verbal assessments of a vital sign of the subject during resuscitation, medications administered to the subject during resuscitation, endotracheal intubation and artificial respiration provided to the subject during resuscitation, vascular accesses (e.g., intravenous lines, intra-osseous lines, arterial lines, and/or other accesses), surgical procedures, laboratory test results associated with the subject, results from point-of-care devices associated with the subject, and/or other information associated with audio information from the environment surrounding the subject.

The code blue documentation may be provided and/or presented in various forms. In some implementations, the code blue documentation may be provided as an electronic document. By way of non-limiting example, the code blue documentation may be exported as a portable document file (PDF) or other electronic document format so that the code blue documentation can be printed for paper chart, or uploaded to an electronic medical record (EMR). The code blue documentation may be provided directly as an electronic medical record.

Figure 5:
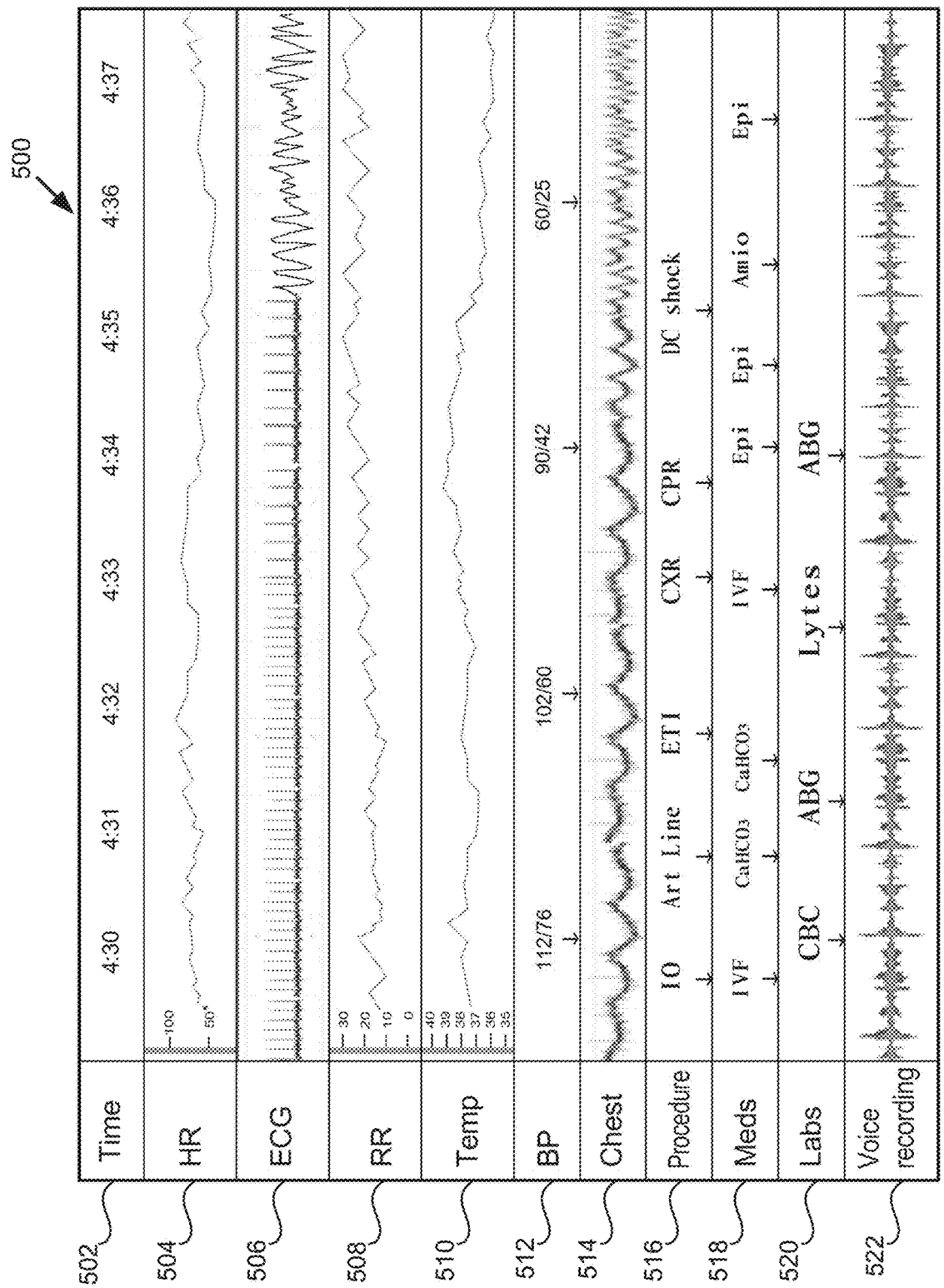
FIG. 5 illustrates a graphical user interface presenting code blue documentation, in accordance with one or more implementations.

In some implementations, the feedback, the code blue documentation, and/or other information may be provided for presentation via portable computing platform 104. FIG. 5 illustrates a graphical user interface 500 presenting code blue documentation, in accordance with one or more implementations. The graphical user interface 500 may be presented by personal computing platform 104. The graphical user interface 500 may include one or more of a time field 502, a heart rate field 504, an ECG field 506, a respiratory rate field 508, a temperature field 510, a blood pressure field 512, an oxygen saturation field ($SpO_2$) (not depicted), a chest movement field 514, a procedure field 516, a medication field 518, a labs field 520, a voice recording field 522, and/or other fields. The fields of graphical user interface 500 presented in FIG. 5 are intended to be illustrative. In some implementations, graphical user interface 500 may include one or more additional fields not described, and/or without one or more of the fields discussed. Additionally, the order and/or arrangement in which the fields of graphical user interface 500 are illustrated in FIG. 5 are not intended to be limiting.

The fields of graphical user interface 500 may be configured to convey various information. The time field 502 may be configured to convey time information associated with a code blue scenario. The time information may include a time of day, a time since the code blue scenario was initiated, a time since apparatus 102 was adhered to the subject, a time since subject collapse, a time since chest compressions were started, and/or other time information associated with the code blue scenario. The heart rate field 504 may be configured to convey the subject's heart rate as a function of time and/or other information associated with the subject's heart rate. The ECG field 506 may be configured to convey the subject's electrocardiogram as a function of time, cardiac rhythm, identifying arrhythmias, and/or other information associated with the subject's ECG. The respiratory rate field 508 may be configured to convey the subject's respiratory rate as a function of time and/or other information associated with the subject's breathing. The temperature field 510 may be configured to convey the subject's temperature as a function of time and/or other information associated with the subject's temperature. The blood pressure field 512 may be configured to convey the subject's blood pressure as a function of time and/or other information associated with the subject's blood pressure. The chest movement field 514 may be configured to convey the subject's chest movements as a function of time and/or other information associated with the subject's chest movements. The procedure field 516 may be configured to convey indications of performed procedures as a function of time, the nature or type of individual procedures, and/or other information associated with procedures performed on the subject. The medication field 518 may be configured to convey indications of provided medications as a function of time, the type and/or dosage of individual medications, and/or other information associate with medications provided to the subject during the code blue scenario. The labs field 520 may be configured to convey indications of performed labs (e.g., assays) as a function of time, the nature or type of individual labs, and/or other information related to labs associated with the code blue scenario. The voice recording field 522 may be configured to convey audio information recorded in the environment surrounding the subject during the code blue scenario. The audio information may be transcribed into text. The graphical user interface 500 may be configured to facilitate audible playback of audio information. In some implementations, graphical user interface 500 may be configured to facilitate zooming in and out of a graphical representation of audio information (e.g., zoom in to view one second of audio information, zoom out to fit the size of a screen, and/or other zoom configurations). In some implementations, graphical user interface 500 may be configured to convey a detailed analysis of chest compressions (e.g., rate, depth, pauses, and intervals). Onscreen calipers may be provided to measure time intervals between events and measure time intervals for one or more quality of care indicators.

In some implementations, one or more of these fields may be configured to display a real-time value for the parameter associated with a given field. For example, the heart rate field 504 may be configured to convey the subject's real-time heart rate. The respiratory rate field 508 may be configured to convey the subject's real-time respiratory rate. The temperature field 510 may be configured to convey the subject's real-time temperature. The blood pressure field 512 may be configured to convey the subject's real-time blood pressure. The chest movement field 514 may be configured to convey the subject's real-time chest movements. These examples are not intended to be limiting.

Turning back to FIG. 1, in some implementations, apparatus 102, personal computing platform 104, server 106, feedback processor 109, and/or external resources 152 may be operatively linked via one or more electronic communication links. For example, such electronic communication links may be established, at least in part, via a network or connection such as the Internet, Wi-Fi, Bluetooth, and/or other networks or connections. It will be appreciated that this is not intended to be limiting, and that the scope of this disclosure includes implementations in which apparatus 102, personal computing platform 104, server 106, feedback processor 109, and/or external resources 152 may be operatively linked via some other communication media.

By way of non-limiting example, a given personal computing platform 104 may include one or more of a desktop computer, a laptop computer, a handheld computer, a tablet computing platform, a NetBook, a Smartphone, and/or other computing platforms.

Server 106 may include electronic storage, one or more processors, and/or other components. Server 106 may be configured to execute computer program instructions 138, computer program instructions 146, and/or other instructions. Server 106 may include communication lines, or ports to enable the exchange of information with a network and/or other computing platforms. Illustration of server 106 in FIG. 1 is not intended to be limiting. Server 106 may include a plurality of hardware, software, and/or firmware components operating together to provide the functionality attributed herein to server 106. For example, server 106 may be implemented by a cloud of computing platforms operating together as server 106.

External resources 152 may include sources of information, hosts and/or providers of medical information (e.g., EMR) outside of system 100, external entities participating with system 100, and/or other resources. In some implementations, some or all of the functionality attributed herein to external resources 152 may be provided by resources included in system 100.

Electronic storage 114 and/or 142 may comprise non-transitory storage media that electronically stores information. The electronic storage media of electronic storage 114 and/or 142 may include one or both of system storage that is provided integrally (i.e., substantially non-removable) with a device (e.g., apparatus 102 or personal computing platform 104) and/or removable storage that is removably connectable to the device (e.g., apparatus 102 or personal computing platform 104), for example, a port (e.g., a USB port, a firewire port, etc.) or a drive (e.g., a disk drive, etc.). Electronic storage 114 and/or 142 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 114 and/or 142 may include one or more virtual storage resources (e.g., cloud storage, a virtual private network, and/or other virtual storage resources). Electronic storage 114 and/or 142 may store software algorithms, information determined by a processor (e.g., processor(s) 109, processor(s) 116, and/or processor(s) 144), information received from server 106, information received from personal computing platforms 104, information received from apparatus 102, information received from feedback processor 109, information received from external resources 152, and/or other information that enables system 100 to function as described herein.

Processor(s) 116 may be configured to provide information processing capabilities in apparatus 102. Processor(s) 144 may be configured to provide information processing capabilities in personal computing platform 104. Feedback processor(s) 109 may be configured to provide information processing capabilities in and/or for either one of these devices, as well as for system 100 as a whole. As such, processor(s) 109, 116, and/or 144 may include one or more of a digital processor, an analog processor, a digital circuit designed to process information, an analog circuit designed to process information, a state machine, and/or other mechanisms for electronically processing information. Although processor(s) 109, 116, and 144 are shown in FIG. 1 as single entities, this is for illustrative purposes only. In some implementations, processor processor(s) 109, 116, and/or 114 may include a plurality of processing units. These processing units may be physically located within the same device, or processor(s) 109, 116, and/or 114 may represent processing functionality of a plurality of devices operating in coordination. For example, parts and/or all of feedback processor (s) 109 may be included in enclosure 108 of apparatus 102, included in personal computing platform 104, included in server 106, and/or included in other components of the system 100. The processor(s) 109, 116, and/or 114 may be configured to execute computer program instructions (e.g., computer program instructions 138 and/or 146, and/or computer program instructions that facilitate generation of feedback for provision to caregivers) by software; hardware; firmware; some combination of software, hardware, and/or firmware; and/or other mechanisms for configuring processing capabilities on processor(s) 109, 116, and/or 114. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although computer program instruction components 140, 148, and 150 are illustrated in FIG. 1 as being implemented within a single processing unit, in implementations in which processor(s) 116 and/or 114 includes multiple processing units, one or more of components 140, 148, and/or 150 may be implemented remotely from the other components. The description of the functionality provided by the different components 140, 148, and/or 150 described herein is for illustrative purposes, and is not intended to be limiting, as any of components 140, 148, and/or 150 may provide more or less functionality than is described. For example, one or more of components 140, 148, and/or 150 may be eliminated, and some or all of its functionality may be provided by other ones of components 140, 148, and/or 150. As another example, processor(s) 116 and/or 114 may be configured to execute one or more additional components that may perform some or all of the functionality attributed below to one of components 140, 148, and/or 150.

Figure 6:
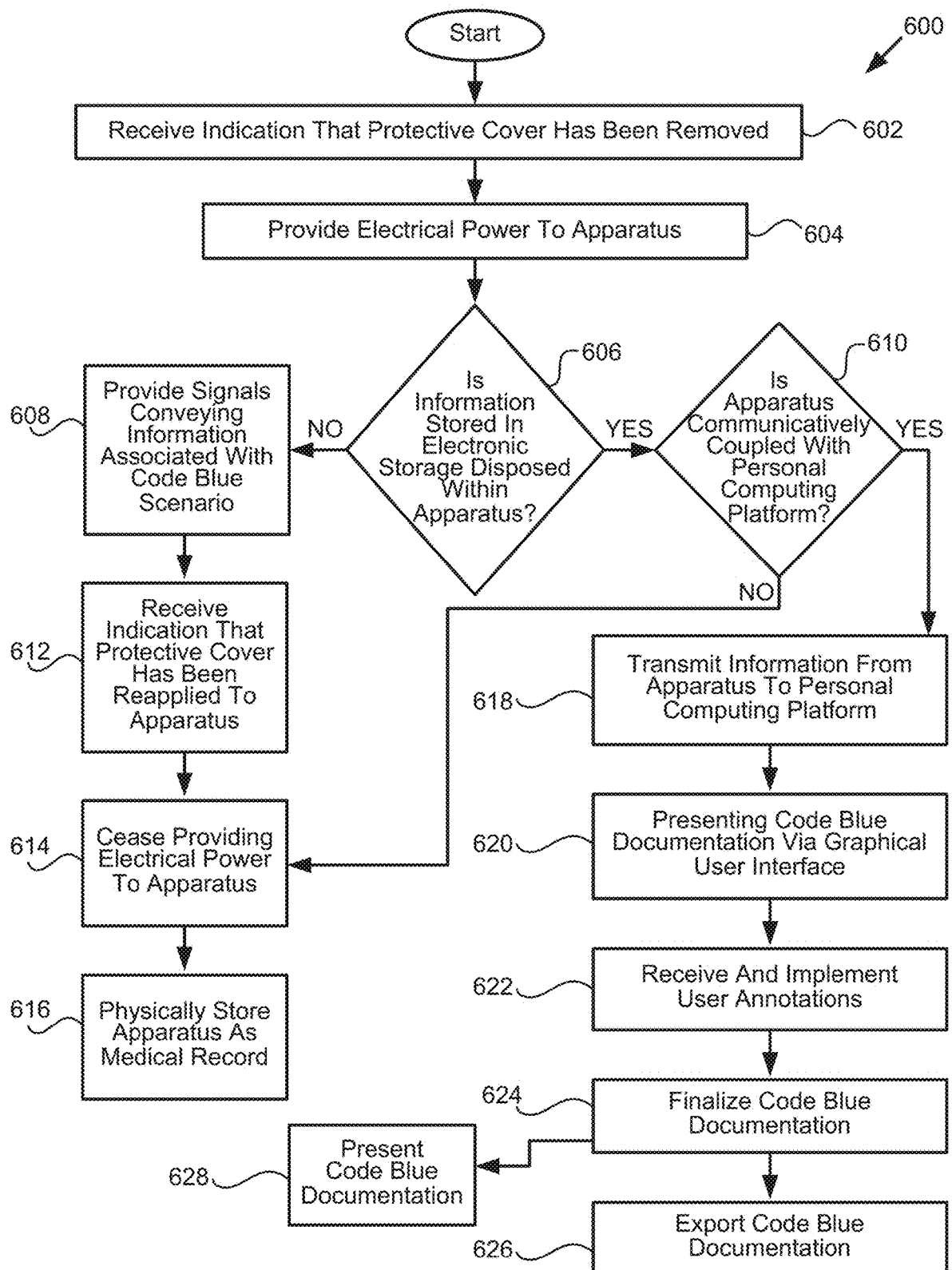
FIG. 6 illustrates a method for documenting code blue scenarios, in accordance with one or more implementations.

FIG. 6 illustrates a method 600 for documenting code blue scenarios, in accordance with one or more implementations.

The operations of method 600 presented below are intended to be illustrative. In some implementations, method 600 may be accomplished with one or more additional operations not described, and/or without one or more of the operations discussed. Additionally, the order in which the operations of method 600 are illustrated in FIG. 6 and described below is not intended to be limiting.

In some implementations, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, an indication may be received conveying that a protective cover has been removed from an apparatus (e.g., apparatus 102) configured to be adhered to the chest of a subject when the code blue scenario begins. In some implementations, operation 602 may be performed by processor(s) 116.

At an operation 604, electrical power may be provided to the apparatus. Operation 604 may be performed by power supply 110, according to some implementations. According to various implementations, the electrical power may be provided responsive to the protective cover being removed and/or the apparatus being applied to the subject.

At an operation 606, electronic storage (e.g., electronic storage 114) disposed within the apparatus may be queried to determine whether information associated with a code blue scenario is stored in the electronic storage. In some implementations, operation 606 may be performed by processor(s) 116. If the determination in operation 606 is positive, method 600 may proceed to an operation 608. If the determination in operation 606 is negative, method 600 may proceed to an operation 610.

At operation 608, a sensor bank (e.g., sensor bank 112) disposed in the apparatus begins providing signals conveying information associated with the code blue scenario, which form a basis for code blue documentation.

At an operation 612, an indication may be received conveying that the protective cover has been reapplied to the apparatus. In some implementations, operation 612 may be performed by processor(s) 116.

At an operation 614, electrical power ceases to be provided to the apparatus. According to various implementations, the electrical power may cease to be provided responsive to the protective cover being reapplied to the apparatus and/or the apparatus being placed into a container.

At an operation 616, the apparatus may be physically stored as a medical record.

Looking back to operation 610, a determination may be made as to whether the apparatus is communicatively coupled with a personal computing platform (e.g., personal computing platform 104). In some implementations, operation 610 may be performed by processor(s) 116 in conjunction with communications interface 118. If the determination in operation 610 is negative, method 600 may proceed to operation 614. If the determination in operation 610 is positive, method 600 may proceed to operation 618.

At operation 618, information associated with the signals provided by the sensor bank may be transmitted from the apparatus to the personal computing platform. In some implementations, operation 618 may be performed by processor(s) 116 in conjunction with communications interface 118.

At an operation 620, the personal computing platform may display a graphical user interface (e.g., graphical user interface 500) presenting code blue documentation. Operation 620 may be performed by processor(s) 144, according to some implementations.

At an operation 622, user annotations may be received by the personal computing platform and implemented in the code blue documentation. Operation 622 may be performed by processor(s) 144, according to some implementations.

At an operation 624, the code blue documentation may be finalized based on one or both of the information received from the apparatus and/or user annotations. Operation 624 may be performed by processor(s) 144, according to some implementations.

At an operation 626, the code blue documentation may be exported in an electronic document format (e.g., PDF). Operation 626 may be performed by processor(s) 144, according to some implementations.

At an operation 628, the code blue documentation may be presented for review of quality, educational purposes, and/or other purposes. Operation 628 may be performed by processor(s) 144, according to some implementations.

Figure 7:
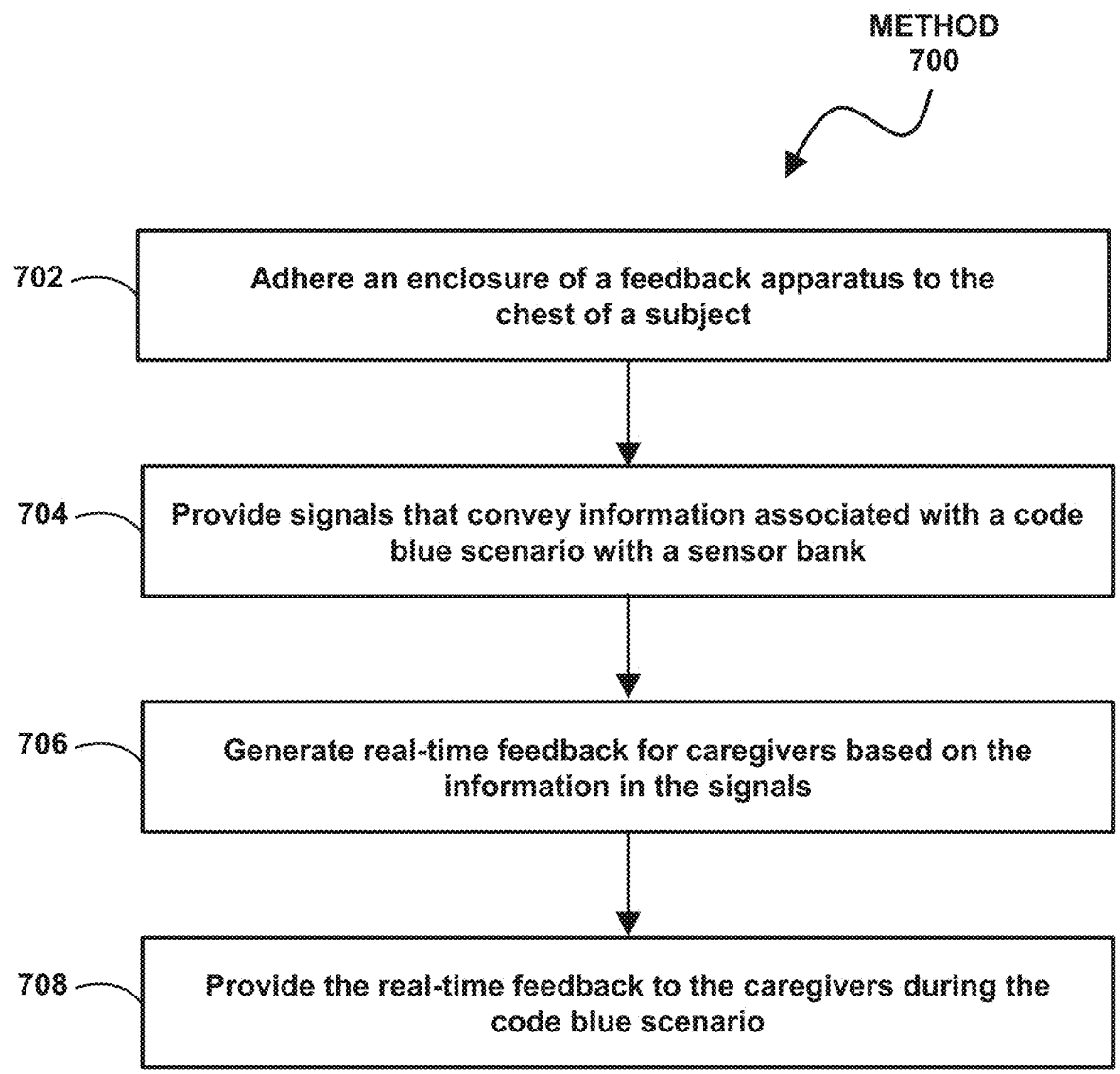
FIG. 7 illustrates a method for providing feedback to caregivers with a feedback apparatus during a code blue scenario, in accordance with one or more implementations.

FIG. 7 illustrates a method 700 for providing feedback to caregivers with a feedback apparatus during a code blue scenario, in accordance with one or more implementations. The system may comprise an enclosure, a sensor bank, a feedback interface, one or more processors, and/or other components. The one or more hardware processors may be configured by computer program instructions. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, the enclosure of the feedback apparatus may be adhered to the chest of a subject. In some implementations, the enclosure may be removably adhered to the skin of the subject's chest. The subject may be undergoing resuscitation. The enclosure may be configured to withstand compressive forces applied to the subject's chest from chest compressions during resuscitation of the subject. Components disposed within the enclosure may be protected from mechanical damage, electrical shock, and/or other conditions. The sensor bank may be at least partially disposed within the enclosure. The feedback interface may be coupled with the enclosure. Operation 702 may be performed by an enclosure the same as or similar to enclosure 108 (shown in FIG. 1 and described herein) according to some implementations.

At an operation 704, signals that convey information associated with the code blue scenario may be provided. The information may include vital signs of the subject during resuscitation, information associated with chest movements of the subject during resuscitation, audio information from an environment surrounding the subject during resuscitation, and/or other information. In some implementations, operation 704 comprises generating, with a heart rate sensor of the sensor bank, a signal conveying information associated with a heart rate of the subject during resuscitation. In some implementations, operation 704 comprises generating, with a cardiac rhythm sensor of the sensor bank, a signal conveying information associated with a cardiac rhythm of the subject during resuscitation. In some implementations, operation 704 comprises generating, with a respiration sensor of the sensor bank, a signal conveying information associated with a respiration of the subject during resuscitation. In some implementations, operation 704 comprises generating, with a chest movement sensor of the sensor bank, a signal conveying information associated with chest movements caused by artificial respiration provided to the subject during resuscitation. In some implementations, operation 704 comprises generating, with a temperature sensor of the sensor bank, a signal conveying information associated with a temperature of the subject during resuscitation. In some implementations, operation 704 comprises generating, with a blood pressure sensor of the sensor bank, a signal conveying information associated with a blood pressure of the subject during resuscitation. In some implementations, operation 704 comprises generating, with an oxygen saturation sensor of the sensor bank, a signal conveying information associated with an oxygen saturation of the subject during resuscitation. In some implementations, operation 704 comprises generating, with a chest compression sensor of the sensor bank, a signal conveying information associated with chest compressions performed on the subject during resuscitation. In some implementations, operation 704 comprises generating, with a cardioversion and/or defibrillation sensor of the sensor bank, a signal conveying information associated with cardioversion procedures and/or defibrillation procedures performed on the subject during resuscitation. In some implementations, operation 704 comprises generating, with a verbal communication sensor of the sensor bank, a signal conveying information associated with verbal communication in an environment of the subject during resuscitation. Operation 704 may be performed by a sensor bank the same as or similar to sensor bank 112 (shown in FIG. 1 and described herein) according to some implementations.

At an operation 706, real time feedback for caregivers may be generated based on the information in the signals and/or other information. The real-time feedback may comprise a recommendation to begin resuscitation, adjustments that should be made to ongoing resuscitation, and/or other feedback. In some implementations, the real-time feedback may comprise adjustments that should be made to ongoing resuscitation. Such adjustments may comprise recommended changes to one or more of a compression rate, a compression depth, a pause between compressions, or a compression interval of cardiopulmonary resuscitation (CPR) chest compressions performed on the subject during the code blue scenario.

In some implementations, generating the real-time feedback based on the information in the signals from the sensor bank may comprise determining time elapsed since a collapse of the subject. The time elapsed since a collapse may be determined to be at least one minute (for example) responsive to the information in the signals from the sensor bank indicating ventricular fibrillation and no respiratory movement in the subject.

In some implementations, the real-time feedback may comprise a recommendation to begin chest compressions on the subject. The recommendation to begin chest compressions on the subject may be determined responsive to the time elapsed since collapse of the subject being at least one minute (for example), the information in the signals from the sensor bank indicating no respiratory movement, the information in the signals from the sensor bank indicating no pulse in the subject, and/or other information. In some implementations, the real-time feedback may comprise a recommendation to shock or defibrillate the subject. The recommendation to shock or defibrillate the subject may be determined responsive to a time elapsed since a start of chest compressions being at least three minutes (for example), the information in the signals from the sensor bank indicating ventricular fibrillation, the information in the signals from the sensor bank indicating no pulse in the subject, and/or other information. In some implementations, the real-time feedback may comprise a recommendation to inject the subject with epinephrine. The recommendation to inject the subject with epinephrine may be determined responsive to a time elapsed since a start of chest compressions being at least five minutes (for example), the information in the signals from the sensor bank indicating ventricular fibrillation, the information in the signals from the sensor bank indicating no pulse in the subject, and/or other information.

In some implementations, the subject may be receiving positive pressure ventilation during the code blue scenario. In such implementations, the real-time feedback may comprise a recommendation to adjust a ventilation pressure, a ventilation rate, and/or other ventilation parameters. The recommendation to adjust the ventilation pressure and/or the ventilation rate may be determined based on information in the signals related to a rate and depth of chest rise in the subject, for example.

In some implementations, generating the real-time feedback based on the information in the signals from the sensor bank may comprise a machine-learning analysis of the information in the signals from the sensor bank. The machine-learning analysis may comprise determining which future actions taken by caregivers during resuscitation would improve a likelihood of recovery from the code blue scenario by the subject. The machine learning analysis may comprise generating the real-time feedback based on the predictions and/or other operations. Operation 706 may be performed by one or more feedback processors the same as or similar to feedback processor 109 (shown in FIG. 1 and described herein) according to some implementations.

At an operation 708, the real-time feedback may be provided to the caregivers during the code blue scenario. Operation 708 may be performed by a feedback interface the same as or similar to feedback interface 113 (shown in FIG. 1 and described herein) according to some implementations. The feedback interface may comprise one or more of a display screen, one or more indicator lights, a speaker, communications components, and/or other components. The real-time feedback may be provided to the caregivers via one or more of a computing platform located remotely from the enclosure, the display screen, the one or more indicator lights, the speaker, and/or the other components. In some implementations, the feedback interface may include a timer. In some implementations, the timer may be activated responsive to one or both of the apparatus being removably adhered to the subject's chest or an adhesive cover being removed from the enclosure, for example.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. An apparatus configured to provide feedback to caregivers for a code blue scenario, the apparatus comprising:
    an enclosure configured to be adhered to a chest of a subject, the enclosure configured to withstand compressive forces applied to the subject's chest from chest compressions for resuscitation of the subject such that components disposed within the enclosure are protected from mechanical damage;
    a sensor bank at least partially disposed within the enclosure, the sensor bank configured to provide signals conveying information associated with the code blue scenario, the information including vital signs of the subject, information associated with chest movements of the subject, and audio information from an environment surrounding the subject;
    a feedback interface coupled with the enclosure, the feedback interface comprising a grid of at least two rows of at least two separated individual indicator lights formed on a surface of the enclosure, the grid configured to be lit in a specific shape with different colors, patterns, intensities, and frequencies to provide real-time feedback to the caregivers for the code blue scenario; and
    one or more processors operatively coupled with the sensor bank and the feedback interface, the one or more processors configured by computer program instructions to control the grid to generate the real-time feedback based on the information in the signals from the sensor bank and prior real-time feedback generated based on information in prior signals from the sensor bank, wherein the real-time feedback comprises a recommendation to begin resuscitation, and adjustments that should be made to ongoing resuscitation, the adjustments including recommended changes to one or more of a compression rate, a compression depth, a pause between compressions, or a compression interval of cardiopulmonary resuscitation (CPR) chest compressions.

2. The apparatus of claim 1, wherein the feedback interface further comprises a display screen and a speaker, and wherein the feedback interface is configured to provide the real-time feedback to the caregivers via the display screen, the grid of separated individual indicator lights, and the speaker.

3. The apparatus of claim 1, wherein the one or more processors are configured such that generating the real-time feedback based on the information in the signals from the sensor bank comprises a machine-learning analysis of the information in the signals from the sensor bank by a trained machine-learning model, the machine-learning model trained using prior physiological data from prior signals and corresponding prior real-time feedback, the machine-learning analysis comprising determining which future actions taken by caregivers during resuscitation would improve a likelihood of recovery from the code blue scenario by the subject, and generating the real-time feedback based on the future actions.

4. The apparatus of claim 1, wherein the enclosure is further configured to removably adhere to skin of the subject's chest.

5. The apparatus of claim 1, wherein the feedback interface includes a timer, the timer comprising a specific number of lit indicator lights that steadily increase over time, and wherein the timer is configured to be activated responsive to one or both of the apparatus being removably adhered to the subject's chest or an adhesive cover being removed from the enclosure.

6. The apparatus of claim 5, wherein the one or more processors are configured such that generating the real-time feedback comprises determining time elapsed since collapse of the subject, the time elapsed since collapse determined to be at least one minute responsive to the information in the signals from the sensor bank indicating ventricular fibrillation and no respiratory movement.

7. The apparatus of claim 6, wherein the one or more processors are configured such that the recommendation to begin chest compressions on the subject is determined responsive to the time elapsed since collapse of the subject being at least one minute, the information in the signals from the sensor bank indicating no respiratory movement, and the information in the signals from the sensor bank indicating no pulse in the subject.

8. The apparatus of claim 7, wherein the one or more processors are configured such that the real-time feedback comprises a recommendation to shock or defibrillate the subject, the recommendation to shock or defibrillate the subject determined responsive to a time elapsed since a start of chest compressions being at least three minutes, the information in the signals from the sensor bank indicating ventricular fibrillation, and the information in the signals from the sensor bank indicating no pulse in the subject.

9. The apparatus of claim 7, wherein the one or more processors are configured such that the real-time feedback comprises a recommendation to inject the subject with epinephrine, the recommendation to inject the subject with epinephrine determined responsive to a time elapsed since a start of chest compressions being at least five minutes, the information in the signals from the sensor bank indicating ventricular fibrillation, and the information in the signals from the sensor bank indicating no pulse in the subject.

10. The apparatus of claim 1, wherein the one or more processors are configured such that the real-time feedback comprises a recommendation to adjust a ventilation pressure and/or a ventilation rate of positive pressure ventilation provided to the subject, the recommendation to adjust the ventilation pressure and/or the ventilation rate determined based on information in the signals related to a rate and depth of chest rise in the subject.

11. The apparatus of claim 1, wherein the sensor bank includes:
    a heart rate sensor configured to provide a signal conveying information associated with a heart rate of the subject;
    a cardiac rhythm sensor configured to provide a signal conveying information associated with a cardiac rhythm of the subject;

a respiration sensor configured to provide a signal conveying information associated with a respiration of the subject;
a chest movement sensor configured to provide a signal conveying information associated with chest movements caused by artificial respiration provided to the subject;
a temperature sensor configured to provide a signal conveying information associated with a temperature of the subject;
a blood pressure sensor configured to provide a signal conveying information associated with a blood pressure of the subject;
an oxygen saturation sensor configured to provide a signal conveying information associated with an oxygen saturation of the subject;
a chest compression sensor configured to provide a signal conveying information associated with chest compressions performed on the subject;
a cardioversion and/or defibrillation sensor configured to provide a signal conveying information associated with cardioversion procedures and/or defibrillation procedures performed on the subject; and
a verbal communication sensor configured to provide a signal conveying information associated with verbal communication in an environment of the subject.

12. The apparatus of claim 1, wherein the one or more of the indicator lights are configured to be lit with different colors, the different colors comprising red, yellow, and green.

13. The apparatus of claim 12, wherein the different colors correspond to different recommended actions.

14. The apparatus of claim 12, wherein the different colors correspond to an intensity level of a recommended action.

15. The apparatus of claim 14, wherein green indicates less intensity, yellow indicates more intensity, and red indicates a highest intensity.

16. The apparatus of claim 1, wherein the grid of separated individual indicator lights is configured to be lit in a specific shape to indicate specific real-time feedback.

17. The apparatus of claim 1, wherein the indicator lights are configured to be individually controlled to blink or flash with specific patterns to indicate specific real-time feedback.

18. A method for providing feedback to caregivers with a feedback apparatus for a code blue scenario, the apparatus comprising an enclosure, a sensor bank, a feedback interface, and one or more processors configured by computer program instructions, the method comprising:
configuring the enclosure to be adhered to a chest of a subject, the enclosure configured to withstand compressive forces applied to the subject's chest from chest compressions for resuscitation of the subject such that components disposed within the enclosure are protected from mechanical damage, wherein the sensor bank is at least partially disposed within the enclosure, and wherein the feedback interface is coupled with the enclosure;
providing signals with the sensor bank that convey information associated with the code blue scenario, the information including vital signs of the subject, information associated with chest movements of the subject, and audio information from an environment surrounding the subject;
generating real-time feedback for the caregivers based on the information in the signals from the sensor bank and prior real-time feedback generated based on information in prior signals from the sensor bank with the one or more processors, the real-time feedback comprising adjustments that should be made to ongoing resuscitation, the adjustments comprising recommended changes to one or more of a compression rate, a compression depth, a pause between compressions, or a compression interval of cardiopulmonary resuscitation (CPR) chest compressions; and
providing the real-time feedback to the caregivers for the code blue scenario with the feedback interface, the feedback interface comprising a grid of at least two rows of at least two separated individual indicator lights formed on a surface of the enclosure, the grid configured to be lit in a specific shape with different colors, patterns, intensities, and frequencies to provide the real-time feedback.

19. The method of claim 18, wherein the feedback interface further comprises a display screen and a speaker, and wherein the real-time feedback is provided to the caregivers via the display screen, the grid of separated individual indicator lights, and the speaker.

20. The method of claim 18, wherein generating the real-time feedback based on the information in the signals from the sensor bank comprises a machine-learning analysis of the information in the signals from the sensor bank by a trained machine-learning model, the machine-learning model trained using prior physiological data from prior signals and corresponding prior real-time feedback, the machine-learning analysis comprising determining which future actions taken by caregivers would improve a likelihood of recovery from the code blue scenario by the subject, and generating the real-time feedback based on the future actions.

21. The method of claim 18, further comprising removably adhering the enclosure to skin of the subject's chest.

22. The method of claim 18, wherein the feedback interface includes a timer, the timer comprising a specific number of lit indicator lights that steadily increase over time, the method further comprising activating the timer responsive to one or both of the apparatus being removably adhered to the subject's chest or an adhesive cover being removed from the enclosure.

23. The method of claim 22, wherein generating the real-time feedback based on the information in the signals from the sensor bank comprises determining time elapsed since collapse of the subject, the time elapsed since collapse determined to be at least one minute responsive to the information in the signals from the sensor bank indicating ventricular fibrillation and no respiratory movement.

24. The method of claim 23, wherein the real-time feedback comprises a recommendation to begin the chest compressions on the subject, the recommendation to begin chest compressions on the subject determined responsive to the time elapsed since collapse of the subject being at least one minute, the information in the signals from the sensor bank indicating no respiratory movement, and the information in the signals from the sensor bank indicating no pulse in the subject.

25. The method of claim 24, wherein the real-time feedback comprises a recommendation to shock or defibrillate the subject, the recommendation to shock or defibrillate the subject determined responsive to a time elapsed since a start of chest compressions being at least three minutes, the information in the signals from the sensor bank indicating ventricular fibrillation, and the information in the signals from the sensor bank indicating no pulse in the subject.

26. The method of claim 24, wherein the real-time feedback comprises a recommendation to inject the subject with epinephrine, the recommendation to inject the subject with epinephrine determined responsive to a time elapsed since a start of chest compressions being at least five minutes, the information in the signals from the sensor bank indicating ventricular fibrillation, and the information in the signals from the sensor bank indicating no pulse in the subject.

27. The method of claim 18, wherein the real-time feedback comprises a recommendation to adjust a ventilation pressure and/or a ventilation rate of positive pressure ventilation provided to the subject, the recommendation to adjust the ventilation pressure and/or the ventilation rate determined based on information in the signals related to a rate and depth of chest rise in the subject.

28. The method of claim 18, further comprising:
    generating, with a heart rate sensor of the sensor bank, a signal conveying information associated with a heart rate of the subject;
    generating, with a cardiac rhythm sensor of the sensor bank, a signal conveying information associated with a cardiac rhythm of the subject;
    generating, with a respiration sensor of the sensor bank, a signal conveying information associated with a respiration of the subject;
    generating, with a chest movement sensor of the sensor bank, a signal conveying information associated with chest movements caused by artificial respiration provided to the subject;
    generating, with a temperature sensor of the sensor bank, a signal conveying information associated with a temperature of the subject;
    generating, with a blood pressure sensor of the sensor bank, a signal conveying information associated with a blood pressure of the subject;
    generating, with an oxygen saturation sensor of the sensor bank, a signal conveying information associated with an oxygen saturation of the subject;
    generating, with a chest compression sensor of the sensor bank, a signal conveying information associated with chest compressions performed on the subject;
    generating, with a cardioversion and/or defibrillation sensor of the sensor bank, a signal conveying information associated with cardioversion procedures and/or defibrillation procedures performed on the subject; and
    generating, with a verbal communication sensor of the sensor bank, a signal conveying information associated with verbal communication in an environment of the subject.

\* \* \* \* \*